United States Patent [19]
Yuan et al.

[11] Patent Number: 6,036,693
[45] Date of Patent: *Mar. 14, 2000

[54] CERVICAL SPINE STABILIZATION METHOD AND SYSTEM

[75] Inventors: Hansen A. Yuan, Fayetteville, N.Y.; Edward C. Benzel, Albuquerque, N.Mex.; Alex Dinello, Palo Alto, Calif.; Michael H. Wefers, South Euclid, Ohio; Aaron C. Smith, Gibsonia, Pa.

[73] Assignee: DePuy Orthopaedics, Inc., Warsaw, Ind.

[*] Notice: This patent is subject to a terminal disclaimer.

[21] Appl. No.: 09/200,996

[22] Filed: Nov. 30, 1998

Related U.S. Application Data

[63] Continuation of application No. 08/656,662, May 31, 1996, Pat. No. 5,843,082.

[51] Int. Cl.[7] .................................................. A61B 17/70
[52] U.S. Cl. .................................. 606/61; 606/69; 606/73
[58] Field of Search .............................. 606/60, 61, 69, 606/70, 71, 72, 73

[56] References Cited

U.S. PATENT DOCUMENTS

| | | | |
|---|---|---|---|
| 4,041,939 | 8/1977 | Hall | 606/61 |
| 4,289,123 | 9/1981 | Dunn | 606/61 |
| 4,484,570 | 11/1984 | Sutter et al. | 606/72 |
| 5,024,213 | 6/1991 | Asher et al. | 606/61 |
| 5,133,717 | 7/1992 | Chopin | 606/61 |
| 5,147,360 | 9/1992 | Dubousset | 606/61 |
| 5,152,303 | 10/1992 | Allen | 128/898 |
| 5,261,911 | 11/1993 | Carl | 606/61 |
| 5,374,267 | 12/1994 | Siegel | 606/61 |
| 5,403,314 | 4/1995 | Currier | 606/61 |
| 5,423,826 | 6/1995 | Coates et al. | 606/96 |
| 5,582,612 | 12/1996 | Lin | 606/61 |

FOREIGN PATENT DOCUMENTS

| | | |
|---|---|---|
| 4434574 | 4/1996 | Germany . |
| 9426193 | 11/1994 | WIPO . |

*Primary Examiner*—Gary Jackson
*Assistant Examiner*—David O. Reip

[57] ABSTRACT

An apparatus for retaining first and second cervical vertebrae of a spinal column in a desired spatial relationship includes a pair of longitudinal members positionable along the spinal column. A first plate connectable to the first vertebra has an inner side surface for engaging an anterior surface of the first vertebra. The first plate interconnects the pair of longitudinal members. First fastener means is engageable with the first plate for connecting the first plate to the first vertebra. The first fastener means has a threaded end portion for engaging the first vertebra. A second plate connectable to the second vertebra has an inner side surface for engaging an anterior surface of the second vertebra. The second plate interconnects the longitudinal members. Second fastener means is engageable with the second plate for connecting the second plate to the second vertebra. The second fastener means has a threaded end portion for engaging the second vertebra.

20 Claims, 15 Drawing Sheets

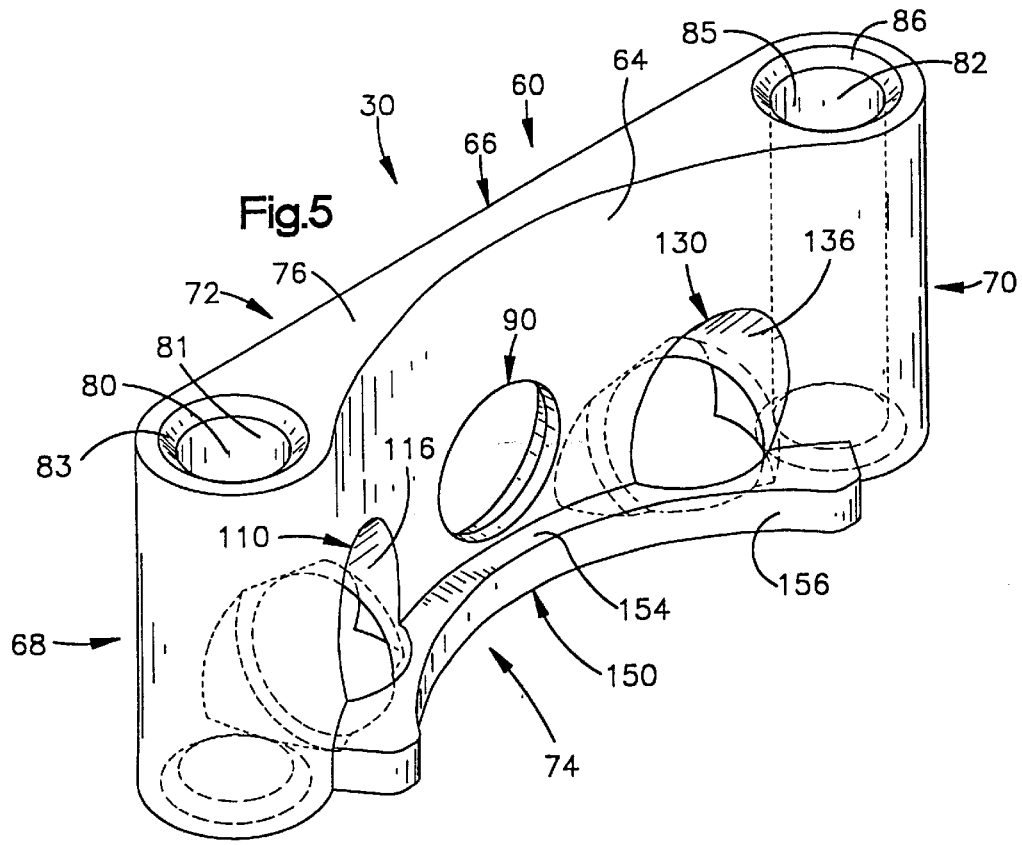
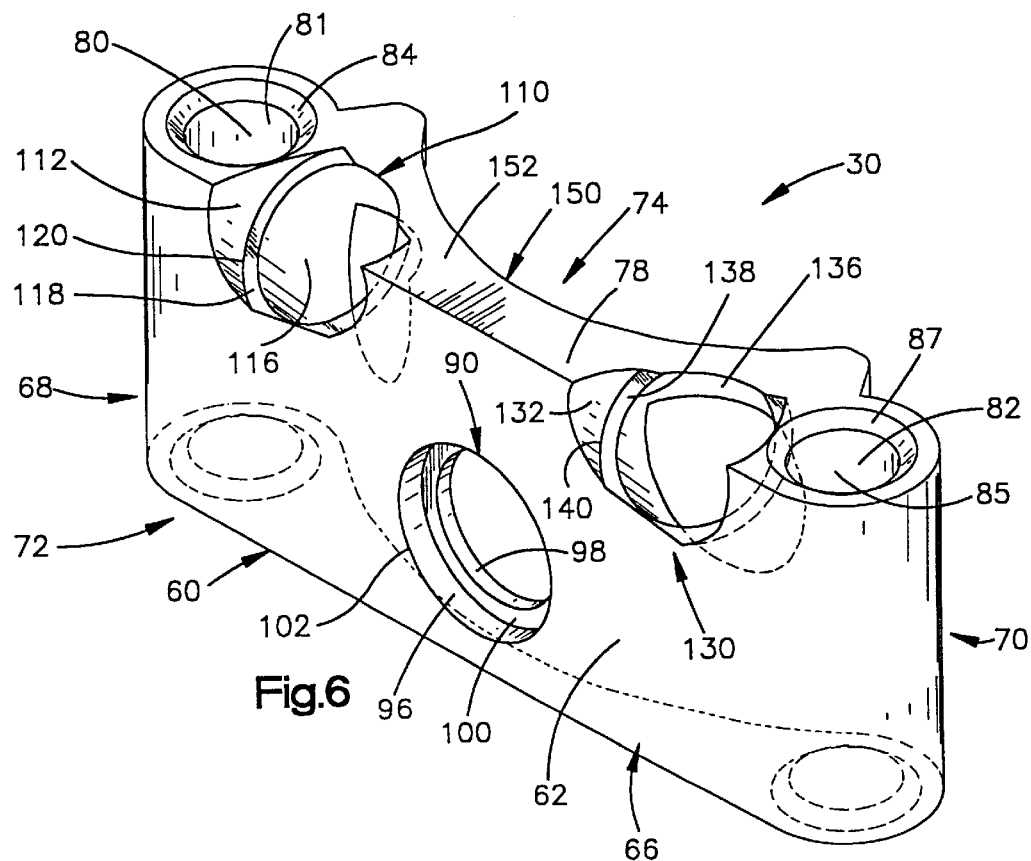

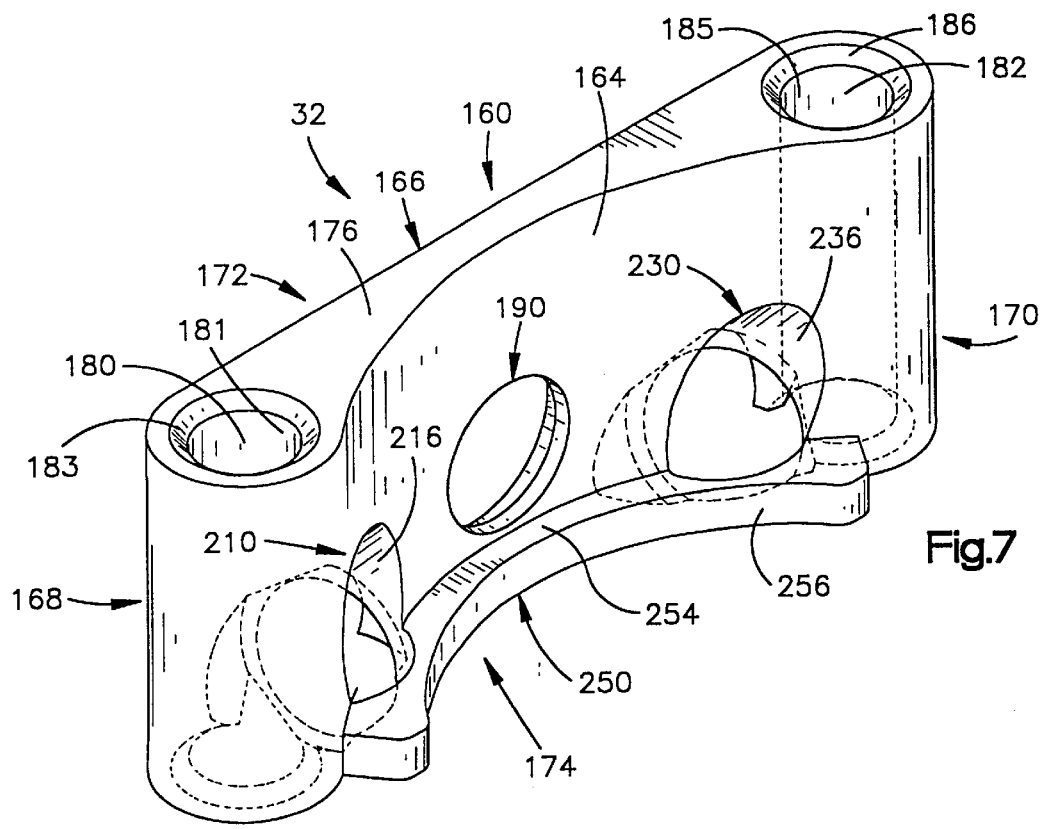
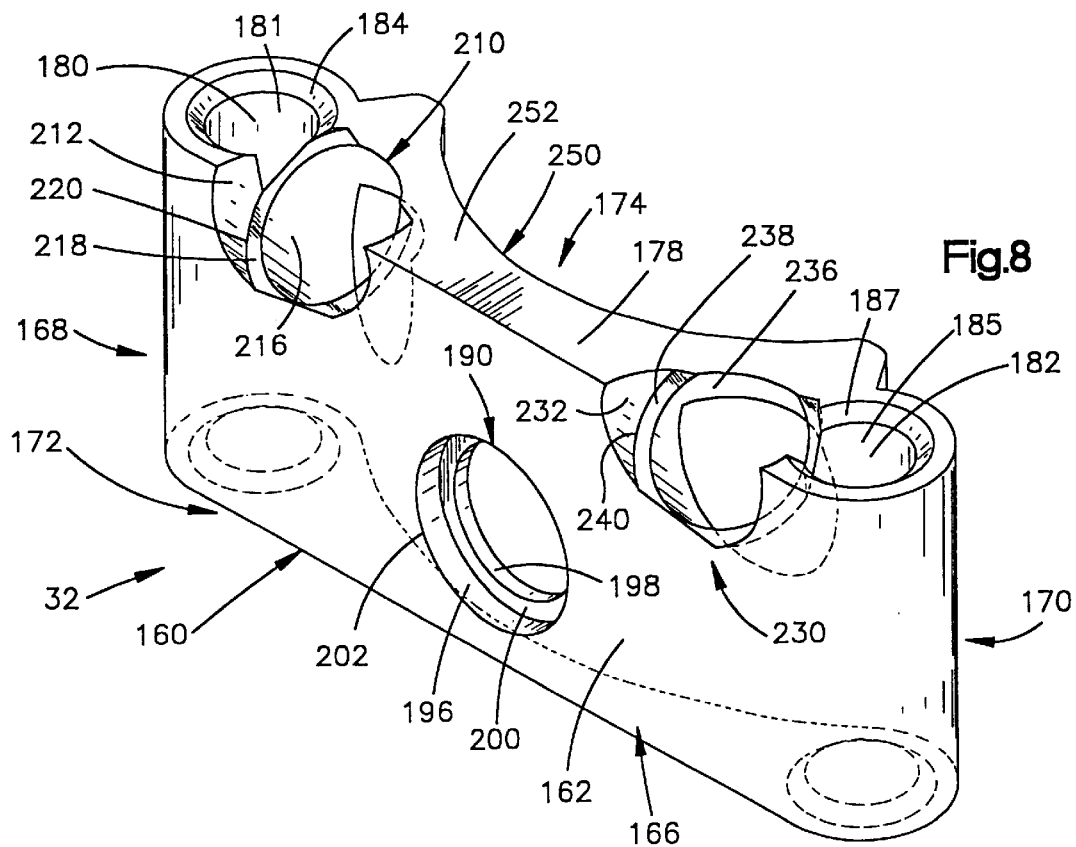

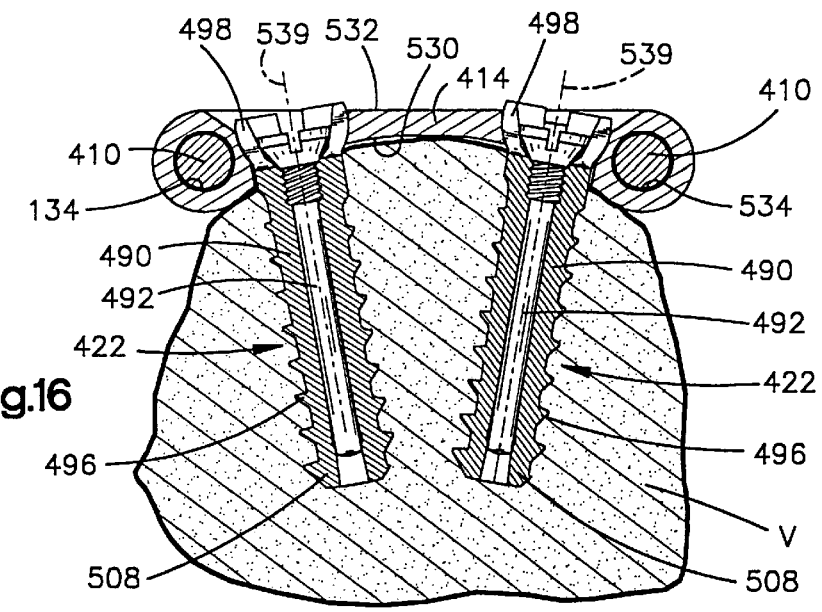
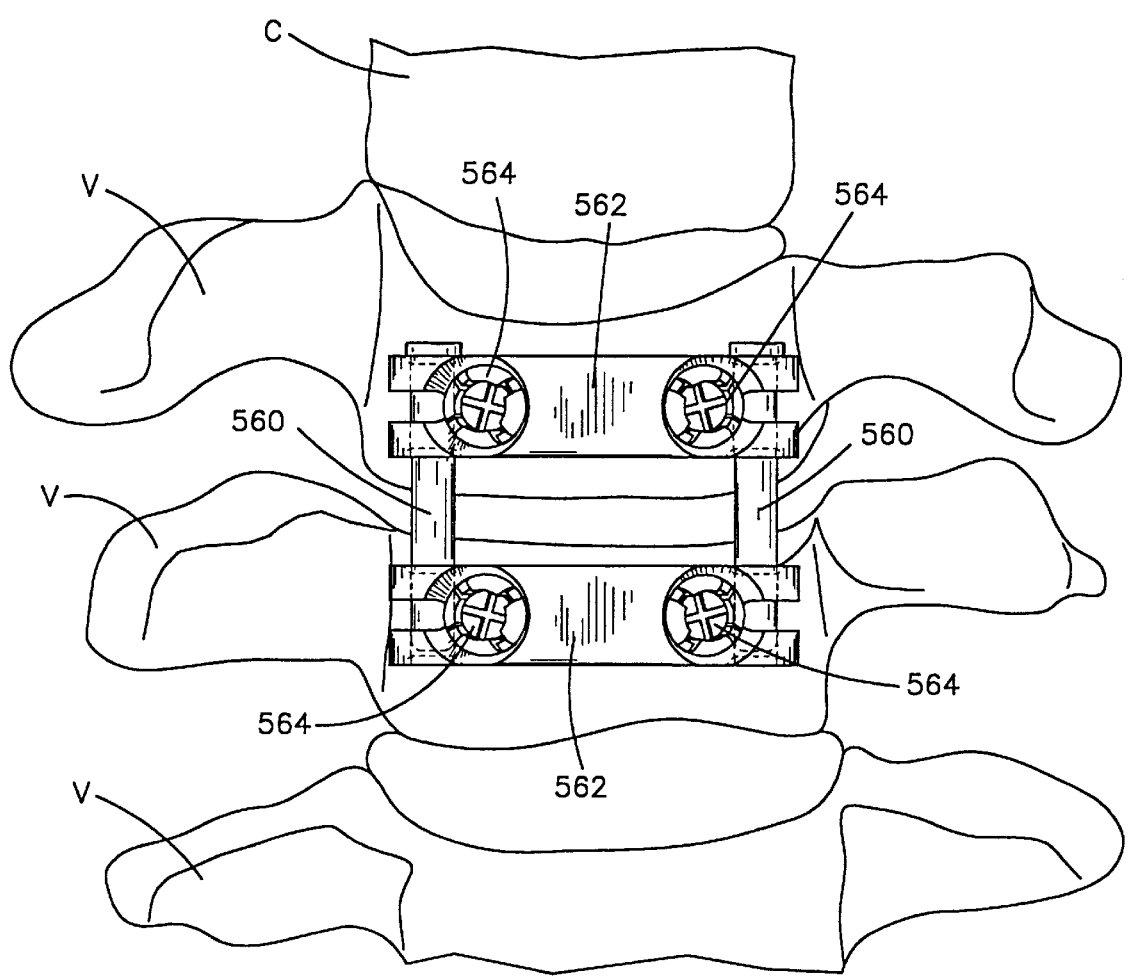

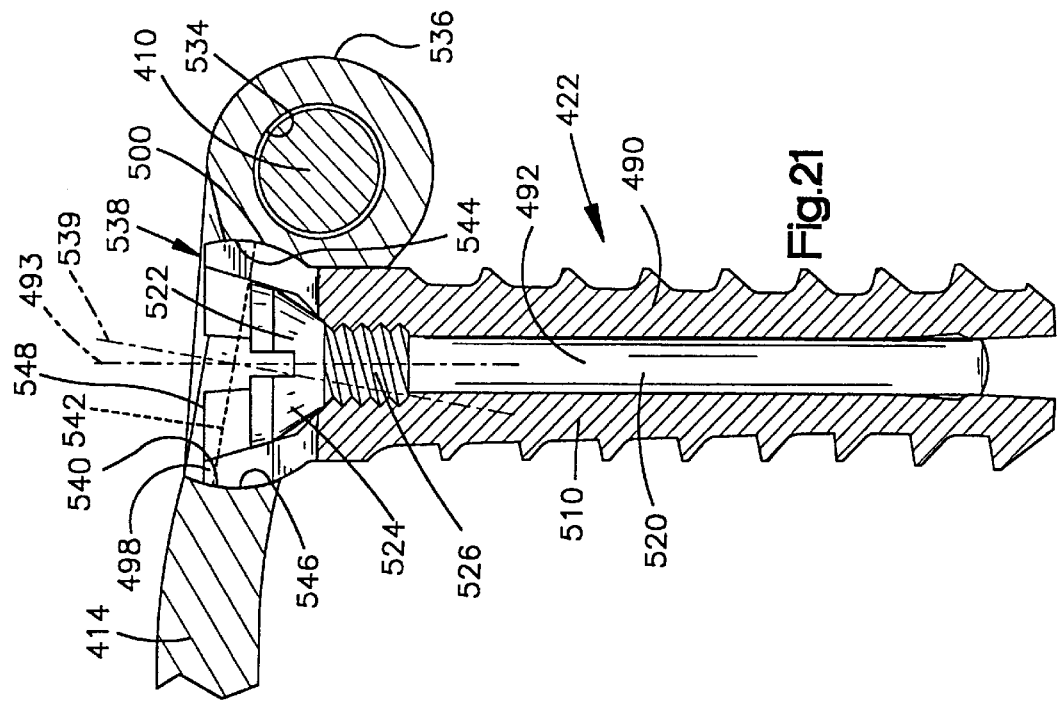
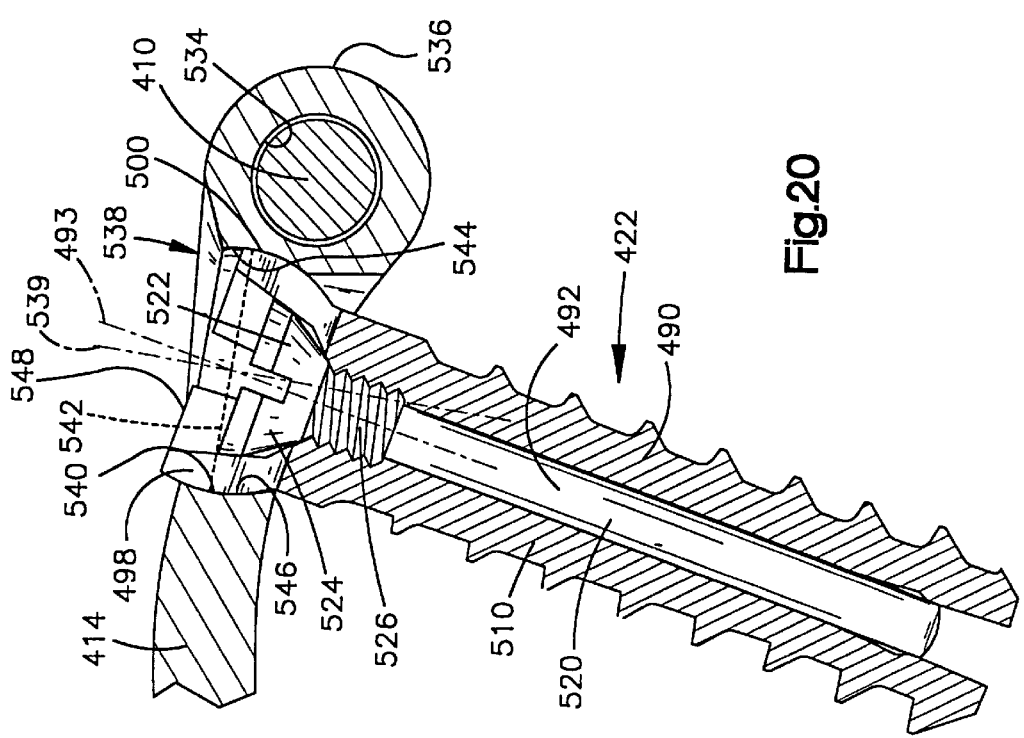

6,036,693

CERVICAL SPINE STABILIZATION METHOD AND SYSTEM

This application is a continuation of application Ser. No. 08/656,662, filed May 31, 1996, now U.S. Pat. No. 5,843,082.

BACKGROUND OF THE INVENTION

1. Technical Field

The present invention relates to an apparatus and method for use in retaining vertebrae of a spinal column in a desired spatial relationship. The present invention is particularly adapted for use in retaining cervical vertebrae of a human spinal column in a desired spatial relationship.

2. Description of the Prior Art

There are various known apparatus for retaining vertebrae of a spinal column in a desired spatial relationship. Certain of such known apparatus include rods connected to and extending between vertebrae and certain of such known apparatus include plates connected to and extending between vertebrae.

SUMMARY OF THE INVENTION

The present invention is an apparatus for retaining first and second vertebrae of a spinal column in a desired spatial relationship. The apparatus comprises a pair of longitudinal members positionable along the spinal column. A first plate is connectable to the first vertebra and interconnects the pair of longitudinal members. First fastener means is engageable with the first plate for connecting the first plate to the first vertebra. The first fastener means has a threaded end portion for engaging the first vertebra. A second plate is connectable to the second vertebra and interconnects the longitudinal members. Second fastener means is engageable with the second plate for connecting the second plate to the second vertebra. The second fastener means has a threaded end portion for engaging the second vertebra. The apparatus is implantable in the body so that, after implantation, the apparatus is entirely within the body.

In accordance with one feature of the present invention, the first and second vertebrae are cervical vertebrae. The first plate has an inner side surface for facing an anterior surface of the first cervical vertebra. The second plate has an inner side surface for facing an anterior surface of the second cervical vertebra.

In accordance with another feature of the present invention, the apparatus includes means for blocking movement of the first plate, which is the lower plate, relative to the longitudinal members. The second plate, which is higher on the spine than the first plate, is movable relative to the longitudinal members along longitudinal axes of the longitudinal members. Since the second plate is movable relative to the longitudinal members, the second vertebra to which the plate is connected is movable relative to the longitudinal members. Thus, bone graft located adjacent the second vertebra carries a load as the bone and bone graft grow together.

In accordance with another feature of the present invention, the apparatus includes means for blocking movement of both the first plate and the second plate relative to the longitudinal members.

The present invention is also a method of retaining first and second vertebrae of a spinal column in a desired spatial relationship. The method comprises the steps of providing a pair of longitudinal members; interconnecting the longitudinal members with a first plate and a second plate; positioning the first plate on the first vertebra with an inner side surface of the first plate facing an anterior surface of the first vertebra while the first plate interconnects the pair of longitudinal members; and positioning the second plate on the second vertebra with an inner side surface of the second plate facing an anterior surface of the second vertebra while the first plate interconnects the pair of longitudinal members. The method also includes the steps of connecting the first plate to the first vertebra by engaging the first plate with a first fastener and threading an end portion of the first fastener into the first vertebra, and connecting the second plate to the second vertebra by engaging the second plate with a second fastener and threading an end portion of the second fastener into the second vertebra.

The present invention is also a method of retaining first and second vertebrae of a spinal column in a desired spatial relationship. The method comprises the steps of positioning a first plate on a first vertebra with an inner side surface of the first plate facing a surface of the first vertebra; positioning a second plate on the second vertebra with an inner side surface of the second plate facing a surface of the second vertebra; and providing a pair of longitudinal members extending between the first and second plates and extending along the spinal column. The method also includes the steps of connecting the first plate to the first vertebra by engaging the first plate with first fastener means and threading an end portion of the first fastener means into the first vertebra; connecting the second plate to the second vertebra by engaging the second plate with second fastener means and threading an end portion of the second fastener means into the second vertebra; and enabling one of the first and second plates to move along the spinal column relative to the pair of longitudinal members and relative to the other one of the first and second plates.

BRIEF DESCRIPTION OF THE DRAWINGS

The foregoing and other features of the present invention will become more apparent to one skilled in the art upon reading the following description of embodiments of the invention with reference to the accompanying drawings, wherein:

FIG. 5 is a perspective view of a first plate which forms a portion of the apparatus of FIG. 1;

FIG. 6 is another perspective view of the plate of FIG. 5;

FIG. 7 is a view similar to FIG. 5 of a second plate which forms a portion of the apparatus of FIG. 1;

FIG. 8 is another perspective view of the plate of FIG. 7;

FIG. 16 is a sectional view, taken generally along the line 16—16 of FIG. 12;

FIG. 20 is an enlarged view, generally similar to FIG. 19, showing another position of the parts of FIG. 17;

FIG. 21 is an enlarged view, generally similar to FIG. 19, showing yet another position of the parts of FIG. 17;

FIG. 22, which is on the drawing sheet with FIG. 16, is a view of a cervical portion of a spinal column with a fifth embodiment of an apparatus constructed in accordance with the present invention connected to anterior portions of the cervical vertebrae to retain a desired spatial relationship between the cervical vertebrae;

DESCRIPTION OF PREFERRED EMBODIMENTS

The present invention relates to an apparatus and method for retaining vertebrae of a spinal column in a desired spatial relationship. The apparatus includes a pair of longitudinal members in the form of rods which are positionable along the spinal column. The apparatus also includes at least a pair of members in the form of plates for interconnecting the rods. Each plate is secured to a respective vertebra by either two or three screws. One of the plates may be a dynamic plate—that is, a plate which is movable relative to the rods when the plate is connected with its associated vertebra. An apparatus which includes a dynamic plate can allow relative movement between vertebrae which are connected by the apparatus.

The present invention is illustrated in association with cervical vertebrae of a human spinal column. It should be understood that vertebrae other than cervical vertebrae of a human spinal column may be retained with the apparatus and method of the present invention.

Figure 1:
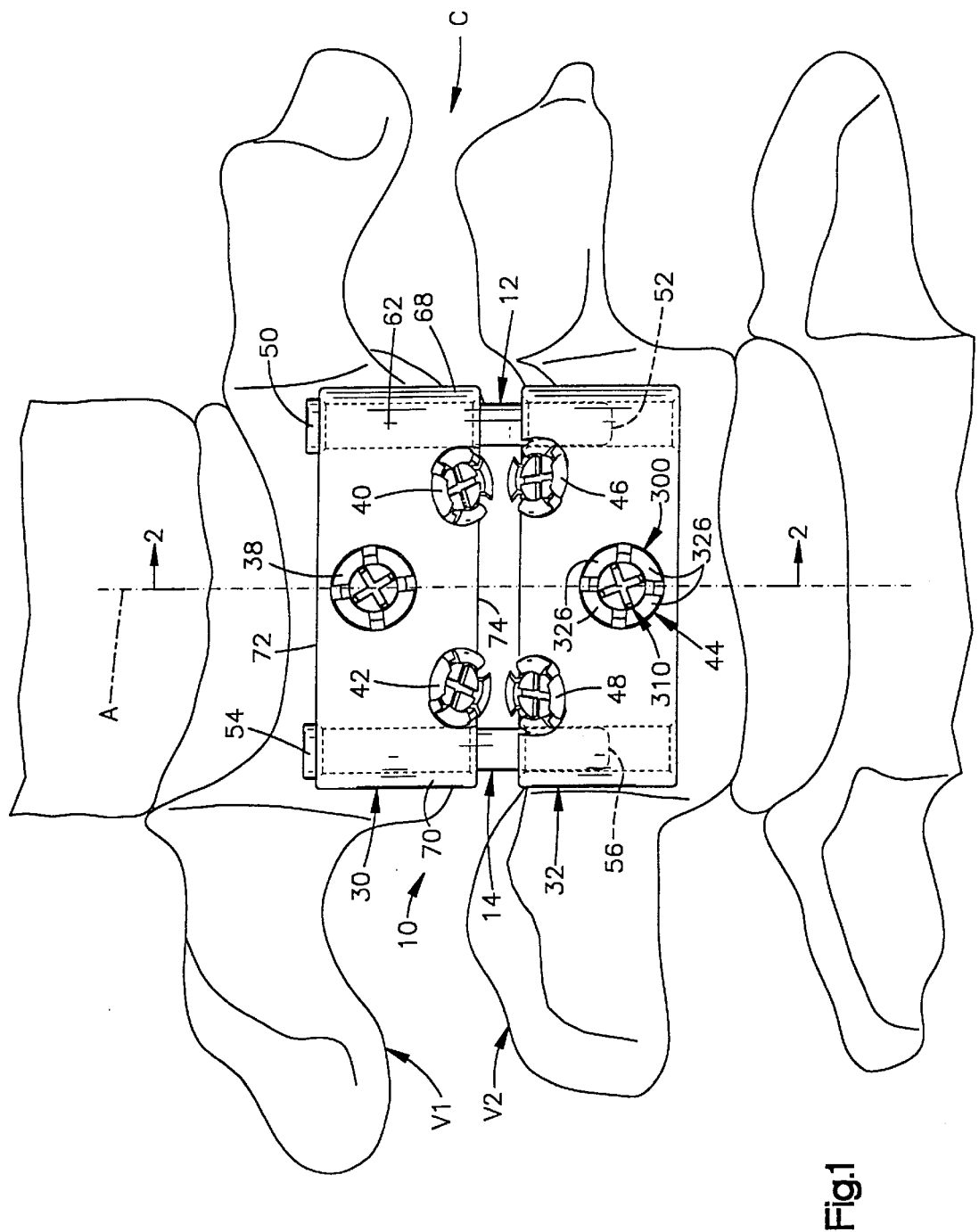
FIG. 1 is an elevational view of an apparatus constructed in accordance with the present invention for maintaining a desired spatial relationship between cervical vertebrae of a spinal column.

As representative of the present invention, FIGS. 1–11 illustrate apparatus which includes rods interconnected by a pair of plates each secured to a respective vertebra by three screws. Specifically, FIG. 1 illustrates an apparatus 10 for use in retaining bone portions such as cervical vertebrae V1 and V2 of a human spinal column C in a desired stabilized spatial relationship. The spinal column C has an axis A which is a vertical axis of the human body.

Figure 2:
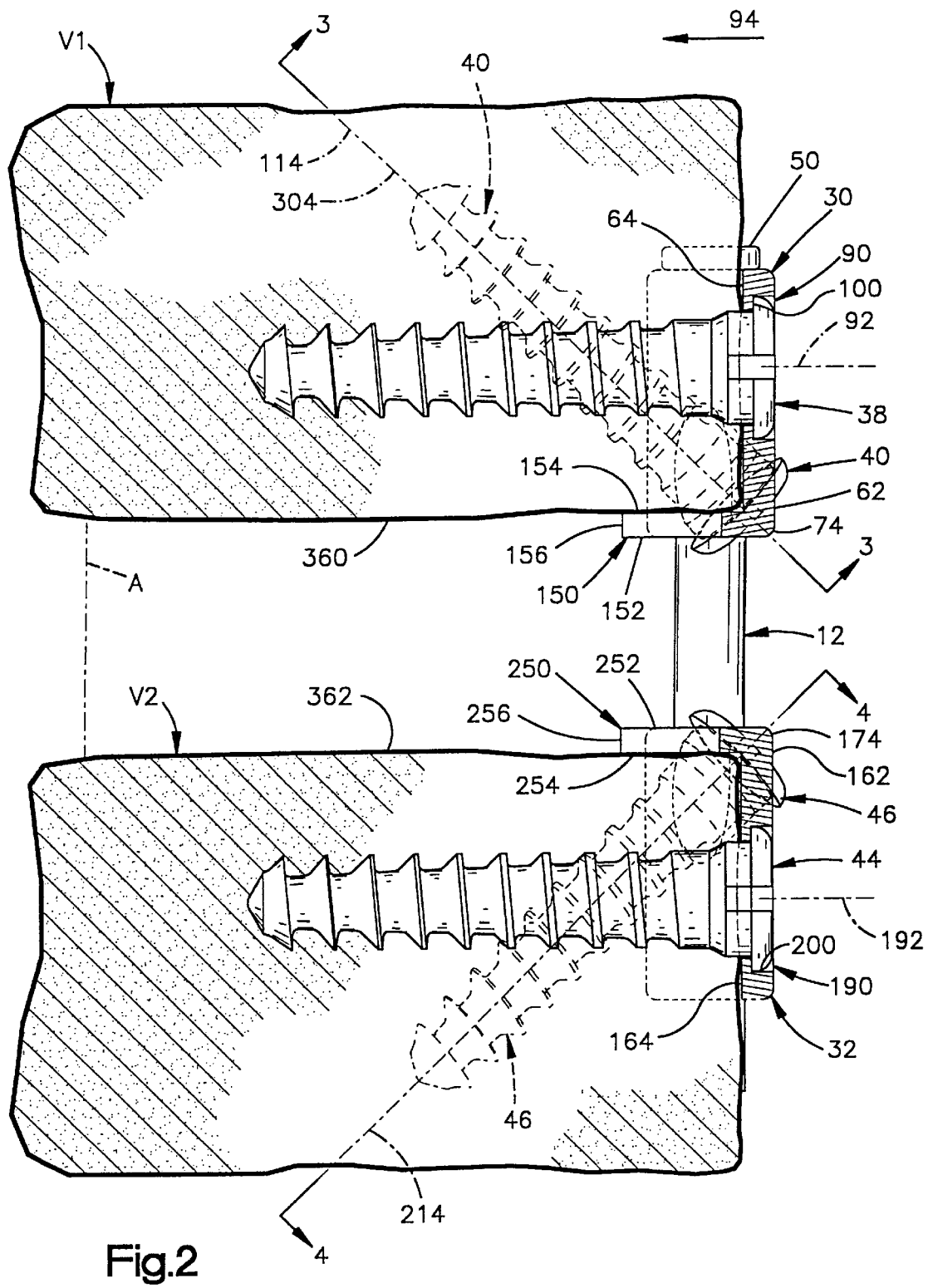
FIG. 2 is a view of the apparatus of FIG. 1, taken along the sagittal plane as indicated by line 2—2 of FIG. 1.
Figure 3:
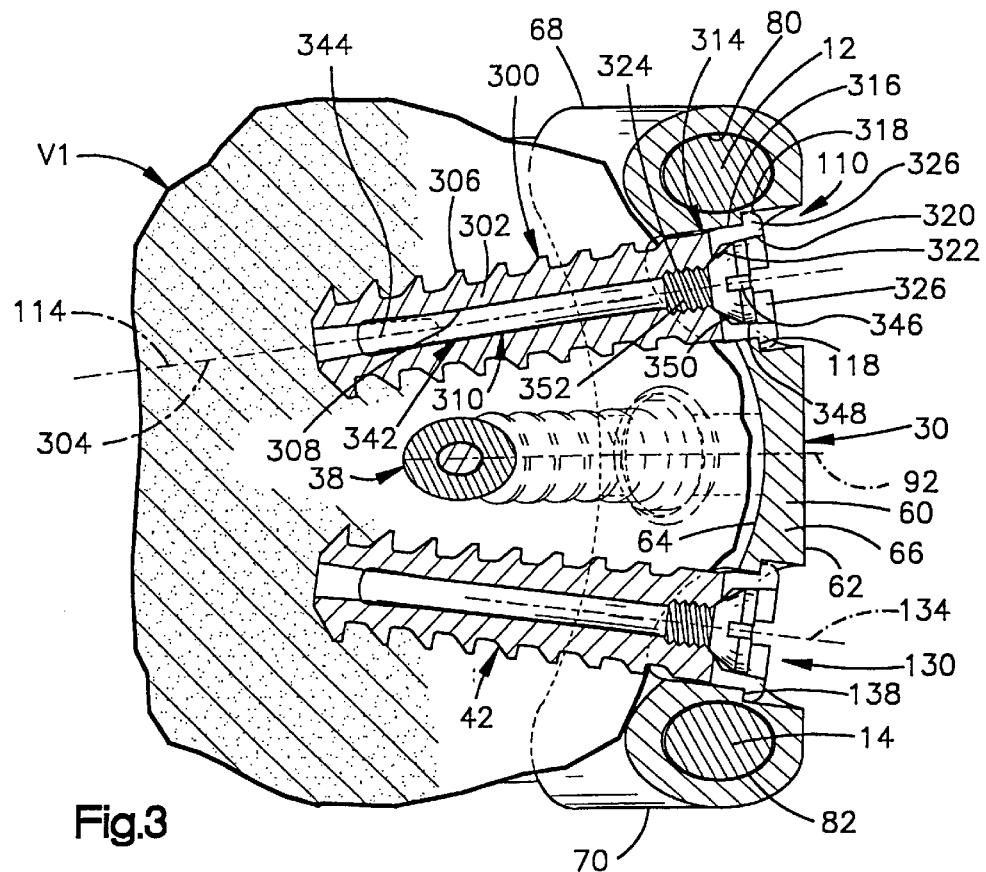
FIG. 3 is a sectional view taken generally along line 3—3 of FIG. 2.
Figure 4:
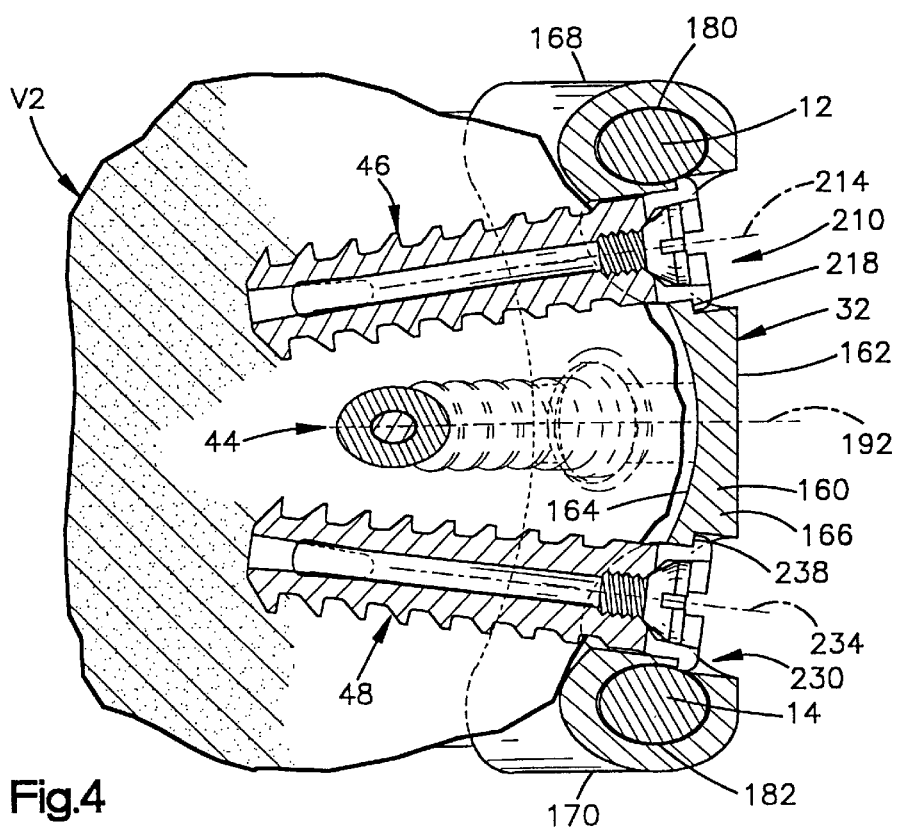
FIG. 4 is a sectional view taken generally along line 4—4 of FIG. 2.

The apparatus 10 includes a pair of surgically implantable rods 12 and 14 (FIGS. 1 and 2). The apparatus 10 also includes first and second members or plates 30 and 32 which engage the rods 12 and 14; three fasteners 38, 40, and 42 for connecting the first plate with the first vertebra V1; and three fasteners 44, 46, and 48 for connecting the second plate with the second vertebra V2.

The first rod 12 (FIG. 1) is made of a suitable biocompatible material, such as titanium or stainless steel. The first rod 12 has an elongate cylindrical configuration and has a circular cross section taken in a plane extending perpendicular to the longitudinal central axis of the first rod. The first rod 12 has a smooth outer surface. A first end portion of the first rod 12 is formed as a cap 50. The first rod 12 also has a second end portion 52 opposite from the first end portion 50. The rod 12 has a uniform diameter of about three (3) millimeters throughout its extent except at the cap 50.

The second rod 14 is identical to the first rod 12. The second rod 14 has a first end portion which is formed as a cap 54. The second rod 14 also has a second end portion 56 opposite from the first end portion 54. The rods 12 and 14 are bendable to a desired configuration to conform to a desired curvature of the spinal column C. The rods 12 and 14 together have sufficient strength and rigidity to maintain the vertebrae V1 and V2 in a desired spatial relationship.

The rods 12 and 14 have a length which is sufficient to enable the rods to span at least the two vertebrae V1 and V2. The length of the rods 12 and 14 will depend upon the condition to be corrected and the number of vertebrae to be held in a desired spatial relationship relative to each other by the apparatus 10. If more than two vertebrae are to be held in a desired spatial relationship relative to each other by the apparatus 10, the rods 12 and 14 would be longer and more than two plates, such as the plates 30 and 32, may be used.

The first plate 30 (FIGS. 5 and 6) is made of a suitable biocompatible material, such as titanium or stainless steel. The first plate 30 includes a main body portion 60. The main body portion 60 of the first plate 30 has a planar outer side surface 62 for facing anteriorly or away from the first vertebra V1. The first plate 30 has an arcuate inner side surface 64 for facing posteriorly or toward the first vertebra V1. The inner side surface 64 of the first plate 30 may engage the anterior surface of the first vertebra V1 when the first plate is connected with the first vertebra as described below.

The main body portion 60 of the first plate 30 has a central portion 66 which extends laterally between a first side portion 68 and a second side portion 70 of the first plate. Because the inner side surface 64 of the first plate 30 has an arcuate configuration, the central portion 66 of the first plate is relatively thin (as viewed in a direction from left to right in FIG. 3) as compared to the first side portion 68 and to the second side portion 70.

The main body portion 60 of the first plate 30 also has first and second end portions 72 and 74. The first end portion 72 of the first plate 30 includes a planar first end surface 76 of the first plate 30. The second end portion 74 includes a planar second end surface 78 of the first plate 30. The second end surface 78 extends parallel to the first end surface 76.

A first rod passage 80 is formed in the first side portion 68 of the first plate 30. The first rod passage 80 is an opening which extends between the first and second end surfaces 76 and 78 of the first plate 30 in a direction parallel to the planar outer side surface 62 of the first plate. The first rod passage 80 is defined by a cylindrical surface 81 and tapered pilot surfaces 83 and 84 at opposite ends of the cylindrical surface 81. The diameter of the cylindrical surface 81 is slightly greater than the diameter of the first rod 12, so that the first rod and the first plate 30 can be relatively movable.

The second side portion 70 of the first plate 30 is a mirror image of the first side portion 68. A second rod passage 82 is formed in the second side portion 70 of the first plate 30. The second rod passage 82 is an opening which extends between the first and second end surfaces 76 and 78 of the first plate 30 in a direction parallel to the planar outer side surface 62 of the first plate. The second rod passage 82 extends parallel to the first rod passage 80. The second rod passage 82 is defined by a cylindrical surface 85 and tapered pilot surfaces 86 and 87 at opposite ends of the cylindrical surface 85. The diameter of the second rod passage 82 is the same as the diameter of the first rod passage 80. The diameter of the cylindrical surface 85 is slightly greater than the diameter of the second rod 14, so that the second rod and the first plate 30 can be relatively movable.

A circular first fastener opening 90 extends through the central portion 66 of the first plate 30. The first fastener opening 90 has an axis 92 (FIG. 2) which extends perpendicular to the plane of the outer side surface 62 of the first plate 30. The axis 92 extends in a first direction as indicated by the arrow 94, that is, from right to left as viewed in FIG. 2, when the first plate 30 is mounted on the first vertebra V1. The first direction 94 extends perpendicular to the axes of the rods 12 and 14.

The first fastener opening 90 is partially defined by a larger diameter cylindrical surface 96 (FIG. 6) which extends from the outer side surface 62 of the first plate 30 in a direction into the material of the central portion 66 of the first plate. The cylindrical surface 96 is centered on the axis 92 of the first fastener opening 90. The first fastener opening 90 is partially defined by a smaller diameter cylindrical surface 98 which extends from the inner side surface 64 of the first plate 30 in a direction into the material of the central portion 66 of the first plate to a location spaced radially inward from the surface 96. The cylindrical surface 98 is centered on the axis 92 of the first fastener opening 90.

An annular shoulder surface 100 (FIGS. 2 and 6) extends radially (relative to the axis 92) between the cylindrical surfaces 96 and 98. The shoulder surface 100 and the larger diameter cylindrical surface 96 define a recess 102 in the outer side surface 62 of the first plate 30.

The main body portion 60 of the first plate 30 also includes a circular second fastener opening 110 formed at a location adjacent to, but spaced apart from, the first rod passage 80 in the first side portion 68 of the first plate. The second fastener opening 110 extends through both the second end surface 78 of the first plate 30 and the outer side surface 62 of the first plate.

The second fastener opening 110 is partially defined by a larger diameter cylindrical surface 112 (FIG. 6) which extends from the outer side surface of the first plate 30 in a direction into the material of the first side portion 68 of the first plate. The cylindrical surface 112 is centered on an axis 114 (FIG. 2) of the second fastener opening 110. The cylindrical surface 112 is spaced apart from the first rod passage 80.

The second fastener opening 110 is partially defined by a smaller diameter cylindrical surface 116 (FIG. 6) which extends from the inner side surface 64 of the first plate 30 in a direction into the material of the first side portion 68 of the first plate, to a location spaced radially inward from the surface 112. The cylindrical surface 116 is centered on the axis 114 of the second fastener opening 110.

An annular shoulder surface 118 (FIGS. 3 and 6) extends radially (relative to the axis 114) between the cylindrical surfaces 112 and 116. The shoulder surface 118 and the larger diameter cylindrical surface 112 define a recess 120 in the outer side surface 62 of the first plate 30.

The axis 114 of the second fastener opening 110 extends transverse to the axis 92 of the first fastener opening 90. Specifically, the axis 114 (FIG. 3) of the second fastener opening 110 converges with the axis 92 of the first fastener opening 90 as viewed in a transverse plane at right angles to the vertical axis A, as can be seen from FIG. 3. In the illustrated embodiment, the axis 114 converges at an angle of about 10° with the axis 92 as viewed in this transverse plane.

The axis 114 of the second fastener opening 110 also converges with the axis 92 of the first fastener opening 90 as viewed in the sagittal plane, as can be seen in FIG. 2. In the illustrated embodiment, the axis 114 converges at an angle of 45° with the axis 92 as viewed in the sagittal plane. It is contemplated that the angle of convergence as viewed in the sagittal plane is preferably in the range of from about 30° to about 60°.

The main body portion 60 of the first plate 30 also includes a circular third fastener opening 130 formed at a location adjacent to, but spaced apart from, the second rod passage 82 in the second side portion 70 of the first plate. The third fastener opening 130 extends through both the second end surface 78 of the first plate 30 and the outer side surface 62 of the first plate.

The third fastener opening 130 is partially defined by a larger diameter cylindrical surface 132 (FIG. 6) which extends from the outer side surface 62 of the first plate 30 in a direction into the material of the second side portion 70 of the first plate. The cylindrical surface 132 is centered on an axis 134 (FIG. 4) of the third fastener opening 130. The cylindrical surface 132 is spaced apart from the second rod passage 82.

The third fastener opening 130 is partially defined by a smaller diameter cylindrical surface 136 (FIG. 6) which extends from the inner side surface 64 of the first plate 30 in a direction into the material of the second side portion 70 of the first plate, to a location spaced radially inward from the surface 32. The cylindrical surface 136 is centered on the axis 134 of the third fastener opening 130.

An annular shoulder surface 138 (FIGS. 3 and 6) extends radially (relative to the axis 134) between the cylindrical surfaces 132 and 136. The shoulder surface 138 and the larger diameter cylindrical surface 132 define a recess 140 in the outer side surface 62 of the first plate 30.

The axis 134 (FIG. 3) of the third fastener opening 130 is coplanar with and extends parallel to the axis 114 of the second fastener opening 110. The axis 134 of the third fastener opening 130 extends transverse to the axis 92 of the first fastener opening 90. Specifically, the axis 134 of the third fastener opening 130 converges with the axis 92 of the first fastener opening 90 as viewed in a transverse plane at right angles to the vertical axis A, as can be seen from FIG. 3. In the illustrated embodiment, the axis 134 converges with the axis 92 at an angle of 10° as viewed in this transverse plane.

The axis 134 of the third fastener opening 130 also converges with the axis 92 of the first fastener opening 90 as viewed in the sagittal plane, as can be seen from FIG. 2. In the illustrated embodiment, the axis 134 converges with the axis 92 at an angle of 45° as viewed in the sagittal plane. It is contemplated that this angle of convergence as viewed in the sagittal plane could be in the range of from about 30° to about 60°.

The first plate 30 includes a lip portion or lip 150 which is formed as one piece with the main body portion 60 of the first plate. The lip 150, best seen in FIGS. 2 and 5, projects from the second end portion 74 of the main body portion 60 of the first plate 30. The lip 150 projects in the first direction 94 (FIG. 2) when the first plate 30 is mounted on the first vertebra V1.

The lip 150 has a planar configuration as viewed in the first direction 94, for example, as seen in FIG. 2. The lip 150 has an arcuate configuration, as can be seen in FIG. 5, when viewed in a direction parallel to the plane of the outer side surface 62 of the first plate 30. The arcuate configuration of the lip 150 generally follows the arcuate configuration of the inner side surface 64 of the main body portion 60 of the first plate 30. The lip 150 extends continuously between the first and second side portions 68 and 70 of the first plate 30. Alternatively, the lip 150 may be discontinuous at one or more locations along the width of the plate 30.

The lip 150 has an outer end surface 152 (FIG. 2) which is formed as an extension of the second end surface 78 of the main body portion 60 of the first plate 30. An opposite inner end surface 154 (FIGS. 2 and 5) of the lip 150 extends parallel to the outer end surface 152. The lip 150 also has an inner side surface 156 which extends between the inner and outer end surfaces 154 and 152 of the lip 150.

The second and third fastener openings 110 and 130 extend partially through the lip 150. The second fastener opening 110, as can be seen in FIG. 2, extends through the corner between, or intersection of, the lip 150 and the main body portion 60 of the first plate 30. The third fastener opening 130 also extends through the corner between, or intersection of, the lip 150 and the main body portion 60 of the first plate 30.

The second plate 32 (FIG. 7) is generally similar in configuration to the first plate 30 (FIG. 5). The second plate 32 (FIG. 7) is configured, however, so that the head ends of fasteners received in certain fastener openings in the second plate are engageable with the rods 12 and 14 disposed in rod passages in the second plate. This engagement can block movement of the second plate 32 relative to the rods 12 and 14, in a manner described below.

The second plate 32 includes a main body portion 160 which has a planar outer side surface 162 for facing anteriorly or away from the vertebra V2. The main body portion 160 also has an arcuate inner side surface 164 for facing posteriorly or toward the second vertebra V2. The inner side surface 164 of the second plate 32 may engage the anterior surface of the second vertebra V2 when the second plate is connected with the second vertebra as described below.

The main body portion 160 has a central portion 166 which extends laterally between a first side portion 168 and a second side portion 170 of the second plate 32. Because the inner side surface 164 of the second plate 32 has an arcuate configuration, the central portion 166 of the second plate 32 is relatively thin (as viewed in a direction from left to right in FIG. 4) as compared to the first side portion 168 and to the second side portion 170.

The main body portion 160 of the second plate 32 also has first and second end portions 172 and 174. The first end portion 172 of the second plate 32 includes a planar first end surface 176 of the second plate. The second end portion 174 of the second plate 32 includes a planar second end surface 178 of the second plate. The second end surface 178 extends parallel to the first end surface 176.

A first rod passage 180 is formed in the first side portion 168 of the second plate 32. The first rod passage 180 is an opening which extends between the first and second end surfaces 176 and 178 in a direction parallel to the planar outer side surface 162 of the second plate 32. The first rod passage 180 is defined by a cylindrical surface 181 and tapered pilot surfaces 183 and 184 at opposite ends of the cylindrical surface 181. The diameter of the cylindrical surface 181 is slightly greater than the diameter of the first rod 12.

A second rod passage 182 is formed in the second side portion 170 of the second plate 32. The second rod passage 182 is an opening which extends between the first and second end surfaces 176 and 178 in a direction parallel to the planar outer side surface 162 of the second plate 32. The second rod passage 182 extends parallel to and has the same diameter as the second rod passage as first rod passage 180. The second rod passage 182 is defined by a cylindrical surface 185 and tapered pilot surfaces 186 and 187 at opposite ends of the cylindrical surface 185. The diameter of the cylindrical surface 185 is slightly greater than the diameter of the second rod 14.

A circular first fastener opening 190 extends through the central portion 166 of the second plate 32. The first fastener opening 190 has an axis 192 (FIGS. 2 and 4) which extends perpendicular to the plane of the outer side surface 162 of the second plate 32. The axis 192 extends in the first direction 94 when the second plate 32 is mounted on the second vertebra V2.

The first fastener opening 190 is partially defined by a larger diameter cylindrical surface 196 (FIG. 8) which extends from the outer side surface 162 of the second plate 32 in a direction into the material of the central portion 166 of the second plate. The cylindrical surface 196 is centered on the axis 192 of the first fastener opening 190. The first fastener opening 190 is partially defined by a smaller diameter cylindrical surface 198 which extends from the inner side surface 164 of the second plate 210 in a direction into the material of the central portion 166 of the second plate, to a location spaced radially inward from the surface 196. The cylindrical surface 198 is centered on the axis 192 of the first fastener opening 190.

An annular shoulder surface 200 (FIGS. 2 and 8) extends radially (relative to the axis 192) between the cylindrical surfaces 196 and 198. The shoulder surface 200 and the larger diameter cylindrical surface 196 define a recess 202 in the outer side surface 162 of the second plate 32.

The main body portion 160 of the second plate 32 also includes a circular second fastener opening 210 formed at a location adjacent to and intersecting the first rod passage 180 in the first side portion 168 of the second plate. The second fastener opening 210 extends through both the second end surface 178 of the second plate 32 and the outer side surface 162 of the second plate.

The second fastener opening 210 is partially defined by a larger diameter cylindrical surface 212 (FIG. 8) which extends from the outer side surface 262 of the second plate 32 in a direction into the material of the first side portion 168 of the second plate. The cylindrical surface 212 is centered on an axis 214 (FIGS. 2 and 4) of the second fastener opening 210. The cylindrical surface 212 intersects the cylindrical surface 181 which defines the first rod passage 180. Thus, the second fastener opening 210 overlaps a portion of the first rod passage 180.

The second fastener opening 210 is partially defined by a smaller diameter cylindrical surface 216 which extends from the inner side surface 264 of the second plate 32 in a direction into the material of the first side portion 168 of the second plate, to a location spaced radially inward from the surface 212. The cylindrical surface 216 is centered on the axis 214 of the second fastener opening 210.

An annular shoulder surface 218 (FIGS. 4 and 8) extends radially (relative to the axis 214) between the cylindrical surfaces 212 and 216. The shoulder surface 218 and the larger diameter cylindrical surface 212 define a recess 220 in the outer side surface 262 of the second plate 32.

The axis 214 of the second fastener opening 210 extends transverse to the axis 192 of the first fastener opening 190. Specifically, the axis 214 of the second fastener opening 210 converges with the axis 192 of the first fastener opening 190 as viewed in a transverse plane at right angles to the vertical axis A, as can be seen from FIG. 4. In the illustrated embodiment, the axis 214 converges with the axis 192 at angle of about 10° as viewed in this transverse plane.

The axis 214 of the second fastener opening 210 also converges with the axis 192 of the first fastener opening 190 as viewed in the sagittal plane, as can be seen in FIG. 2. In the illustrated embodiment, the axis 214 converges with the axis 192 at an angle of 45° as viewed in the sagittal plane. It is contemplated that this angle of convergence could be in the range of from about 30° to about 60° as viewed in the sagittal plane.

The main body portion 160 of the second plate 32 also includes a circular third fastener opening 230 formed at a location adjacent to and intersecting the second rod passage 182 in the second side portion 170 of the second plate. The third fastener opening 230 extends through both the second end surface 178 of the second plate 32 and the outer side surface 162 of the second plate. The distance between the third fastener opening 230 in the second plate 32 and the second fastener opening 210 in the second plate is slightly more than the distance between the third fastener opening 130 in the first plate 30 and the second fastener opening 110 in the first plate.

The third fastener opening 230 is partially defined by a larger diameter cylindrical surface 232 (FIG. 8) which extends from the outer side surface 262 of the second plate 32 in a direction into the material of the second side portion 170 of the second plate. The cylindrical surface 232 is centered on an axis 234 (FIG. 4) of the third fastener opening 230. The cylindrical surface 232 intersects the cylindrical surface 185 which defines the second rod passage 182. Thus, the third fastener opening 230 overlaps a portion of the second rod passage 182.

The third fastener opening 230 is partially defined by a smaller diameter cylindrical surface 236 (FIG. 8) which extends from the inner side surface 264 of the second plate 32 into the material of the second side portion 170 of the second plate to a location spaced radially inward from the surface 232. The cylindrical surface 236 is centered on the axis 234 of the third fastener opening 230.

An annular shoulder surface 238 (FIGS. 4 and 8) extends radially (relative to the axis 234) between the cylindrical surfaces 232 and 236. The shoulder surface 238 and the larger diameter cylindrical surface 232 define a recess 240 in the outer side surface 162 of the second plate 32.

The axis 234 of the third fastener opening 230 is coplanar with and extends parallel to the axis 214 of the second fastener opening 210. The axis 234 of the third fastener opening 230 extends transverse to the axis 192 of the first fastener opening 190. Specifically, the axis 234 of the third fastener opening 230 converges with the axis 192 of the first fastener opening 190 as viewed in a transverse plane at right angles to the vertical axis A, as can be seen from FIG. 4. In the illustrated embodiment, the axis 234 converges with the axis 192 at an angle of about 10° as viewed in this transverse plane.

The axis 234 of the third fastener opening 230 also converges with the axis 192 of the first fastener opening 190 as viewed in the sagittal plane, as can be seen from FIG. 2. In the illustrated embodiment, the axis 234 converges with the axis 192 at an angle of 45°. It is contemplated that this angle of convergence as viewed in the sagittal plane could be in the range of from about 30° to about 60°.

The second plate 32 includes a lip portion or lip 250 which is formed as one piece with the main body portion 160 of the second plate. The lip 250, best seen in FIGS. 4 and 7, projects from the second end portion 174 of the main body portion 160 of the second plate 32. The lip 250 projects in the first direction 94 (FIG. 2) when the second plate 32 is mounted on the second vertebra V2.

The lip 250 has a planar configuration as viewed in the first direction 94, for example, as seen in FIG. 2. The lip 250, as viewed in a direction parallel to the plane of the outer side surface 162 of the second plate 32, has an arcuate configuration generally following the arcuate configuration of the inner side surface 164 of the main body portion 160 of the second plate 32. The lip 250 extends continuously between the first and second side portions 168 and 170 of the second plate 32. Alternatively, the lip 250 may be discontinuous at one or more locations along the width of the second plate 32.

The lip 250 has an outer end surface 252 (FIG. 2) which is formed as an extension of the second end surface 178 of the main body portion 160 of the second plate 32. An opposite inner end surface 254 (FIGS. 2 and 8) of the lip 250 extends parallel to the outer side surface 252. The lip 250 also has an inner side surface 256 which extends between the inner and outer end surfaces 252 and 254 of the lip 250. The second and third fastener openings 210 and 230 extend partially through the lip 250. The second fastener opening 210, as well as the third fastener opening 230, extend through the corner between, or intersection of, the lip 250 and the main body portion 160 of the second plate 32.

The fasteners 38, 40, 42, 44, 46, and 48, which connect the first plate 30 with the first vertebra V1 and the second plate 32 with the second vertebra V2, are identical to each other. Because the fasteners 38–48 are identical, only the fastener 40 is described herein in detail.

The fastener 40 (FIG. 3) includes a sleeve 300 and an expander 310. The sleeve 300 has a hollow, elongate shank portion 302 centered on a longitudinal central axis 304 of the fastener 40. The shank portion 302 defines a cylindrical central opening 308 in the sleeve 300. A coarse external helical thread convolution 306 is formed on the outer peripheral surface of the shank portion 302 of the sleeve 300.

The shank portion 302 of the sleeve 300 is radially and axially slotted so that the shank portion is expandable radially. A series of projections (not shown) are formed on the inner surface of the sleeve 300 for engagement by the expander 310 to expand the shank portion 302 of the sleeve in a manner described below.

A head end portion 314 of the sleeve 300 has a cylindrical outer side surface 316. An annular lip or rim 318 extends around the head end portion 314 of the sleeve 300 and projects radially outward from the outer side surface 316. The head end portion 314 of the sleeve 300 has a conical inner side surface 320 and a conical inner side surface 322. The conical inner side surface 322 merges with an internal thread convolution 324 formed on the sleeve 300.

The head end portion 314 of the sleeve 300 is radially and axially slotted to define four segments 326 of the head end portion. The four segments 326 are movable radially relative to each other and to the axis 304 of the fastener 40 so that the head end portion 314 of the sleeve 300 is expandable radially.

The expander 310 has a head end portion 340 and a shank portion 342. An inner end 344 of the shank portion 342 of the expander 310 is slightly larger in diameter than the cylindrical central opening 308 in the sleeve 300.

The head end portion 340 of the expander 310 has an X-shaped driver slot 346 for receiving a driving tool for rotating the expander relative to the sleeve 300. The head end portion 340 has a conical outer side surface 348 and a conical outer side surface 350. The conical outer side surface 350 on the head end portion 340 of the expander 310 has a different angle of taper than does the conical inner side surface 322 on the head end portion 314 of the sleeve 300.

The conical outer side surface 350 on the head end portion 340 of the expander 310 merges with an external thread convolution 352 formed on the expander 310. The external thread convolution 352 on the expander 310 screws into the internal thread convolution 324 on the sleeve 300.

To install (implant) the apparatus 10 on the spinal column C, the rods 12 and 14 may first be assembled with the plates 30 and 32. Specifically, the first rod 12 is inserted through the first rod passage 80 in the first plate 30 and through the first rod passage 180 in the second plate 32. One of the tapered pilot surfaces 83 and 84 on the first plate 30, and one of the tapered pilot surfaces 183 and 184 on the second plate 32, guide insertion of the first rod 12. The second rod 12 is inserted through the second rod passage 82 in the first plate 30 and through the second rod passage 182 in the second plate 32. One of the tapered pilot surfaces 86 and 87 on the first plate 30, and one of the tapered pilot surfaces 186 and 187 on the second plate 32, guide insertion of the second rod 14.

The assembly of the rods 12 and 14 and the plates 30 and 32 is then positioned over the exposed anterior surface of the spinal column C. The first plate 30 (FIG. 2) is positioned adjacent to the first vertebra V1 so that the first end surface 154 on the lip 150 of the first plate engages a lower surface 360 on the first vertebra V1. The lower surface 360 on the first vertebra V1 faces toward the second vertebra V2. The second plate 32 is positioned adjacent to the second vertebra V2 so that the first end surface 254 on the lip 250 of the second plate engages an upper surface 362 on the second vertebra V2. The upper surface 362 on the second vertebra V2 faces toward the first vertebra V1.

With the first plate 30 on the first vertebra V1, and the second plate 32 on the second vertebra V2, a suitable drill guide and drill (not shown) are used to drill fastener openings in the first vertebra V1 and in the second vertebra V2.

The fasteners 38, 40 and 42 are inserted to connect the first plate 30 with the first vertebra. The insertion and securing of the fastener 40, although not necessarily performed first, will be described as exemplary.

The sleeve 300 of the fastener 40 is inserted through the second fastener opening 110 in the first plate 30. The sleeve 300 of the fastener 40 is threaded into the drilled opening in the vertebra V1 in a known manner (not shown) to fix the sleeve in position in the vertebra V1. The unexpanded head portion 314 of the sleeve 300 is disposed in the recess 120 in the first plate 30.

The expander 310 of the fastener 40 is then inserted into the sleeve 300. The externally threaded portion 352 of the expander 310 is screwed into the internal threads 324 on the sleeve 300. When the expander 310 is fully screwed into the sleeve 300, the inner end portion 344 of the expander 310 causes the shank portion 302 of the sleeve to expand radially outward, helping to lock the sleeve in place in the vertebra V1. When the expander 310 is fully screwed into the sleeve 300, the head portion 340 of the expander 310 engages the head portion 314 of the sleeve 300. The head portion 340 of the expander 310 wedges the locking segments 326 on the sleeve 300 radially outward into engagement with the first plate 30 to rigidly lock the fastener 40 in position relative to the first plate. The head of the fastener 40 is adjacent to the lip 150.

The remaining fasteners 38 and 42 for the first plate 30 are similarly secured to the vertebra V1 and are rigidly locked to the first plate. The heads of the fasteners 38 and 42 are adjacent to the lip 150. As a result, the first plate 30 is securely connected with the first vertebra V1.

The fasteners 44, 46 and 48 are similarly used to connect the second vertebra V2 and the second plate 32. The heads of the fasteners 44, 46 and 48 are adjacent to the lip 250. As a result, the fasteners 44, 46 and 48 are rigidly locked to the second plate 32 and the second plate 32 is securely connected with the second vertebra V2.

As can be seen in FIG. 2, the fastener 40 (as well as the fastener 42, not shown in FIG. 2) extends at an angle (upward as viewed in FIG. 2) to the lip 150. Accordingly, when the fasteners 40 and 42 are tightened into the first vertebra V1, the fasteners tend to draw the lip 150 of the first plate 30 tightly against the surface 360 of the vertebra, that is, in an upward direction as viewed in FIG. 2. At the same time, the fasteners 40 and 42, as well as the fastener 38, tend to draw the main body portion 60 of the first plate 30 tightly against the anterior surface of the first vertebra V1, that is, in a direction to the left as viewed in FIG. 2. Accordingly, it can be seen that tightening the fasteners 38, 40 and 42 tends to draw the first plate 30 in two directions against the first vertebra V1.

The first fastener 38 has a longitudinal central axis which is coincident with the axis 92 of the first fastener opening 90 when the first fastener 38 is disposed in the first fastener opening 90 in the first plate 30. When the second fastener 40 is disposed in the second fastener opening 110 in the first plate 30, the longitudinal central axis 304 of the second fastener 40 is coincident with the axis 114 of the second fastener opening 110.

As described above, the axis 92 of the first fastener opening 90 and the axis 114 of the second fastener opening 110 converge at an acute angle as viewed in the sagittal plane (FIG. 2). Therefore, the longitudinal axis of the first fastener 38 and the longitudinal axis 304 of the second fastener 40 converge at an acute angle as viewed in the sagittal plane (FIG. 2) when the first and second fasteners 38 and 40 connect the first plate 30 with the first vertebra V1. In the illustrated embodiment, the axis of the first fastener 38 and the axis 304 of the second fastener 40 converge at an angle of about 45° as viewed in the sagittal plane. It is contemplated that this angle of convergence in the sagittal plane is preferably in the range of from about 30° to about 60°.

When the third fastener 42 is disposed in the third fastener opening 130 in the first plate 30, the longitudinal central axis of the third fastener 42 is coincident with the axis 134 of the third fastener opening 130. As described above, the axis 92 of the first fastener opening 90 and the axis 134 of the third fastener opening 110 converge at an acute angle as viewed in the sagittal plane (FIG. 2). Therefore, the longitudinal axis of the first fastener 38 and the longitudinal axis of the third fastener 42 converge at an acute angle as viewed in the sagittal plane (FIG. 2) when the first and third fasteners 38 and 42 connect the first plate 30 with the first vertebra V1. In the illustrated embodiment, the axis of the first fastener 38 and the axis of the third fastener 42 converge at an angle of about 45° as viewed in the sagittal plane. It is contemplated that this angle of convergence in the sagittal plane is preferably in the range of from about 30° to about 60°.

The second plate 32 is, in a similar manner, secured in position relative to the second vertebra V2. Tightening the fasteners 44, 46 and 48 tends to draw the second plate 32 in two directions against the second vertebra V2.

When the first fastener 44, the second fastener 46, and the third fastener 48 connect the second plate 32 with the second vertebra V2, the axis of the first fastener 44 and the axis of the second fastener 46 converge at an acute angle as viewed in the sagittal plane (FIG. 2). Also, the axis of the first fastener 44 and the axis of the third fastener 48 converge at an acute angle as viewed in the sagittal plane (FIG. 2). In the illustrated embodiment, these axes converge at an angle of about 45° as viewed in the sagittal plane. It is contemplated that this angle of convergence in the sagittal plane could be in the range of from about 30° to about 60°.

The fact that there are three screws which secure each one of the plates 30 and 32 to the spinal column C also helps to maintain proper placement of the plates. These features help the apparatus 10 maintain the vertebrae V1 and V2 in place when the cervical spine is subjected to various degrees of motion of the human head.

When the second plate 32 is being connected with the second vertebra V2, the outer fasteners 46 and 48 secure the second plate and the second vertebra. The fasteners 46 and 48 also serve to interlock the second plate 32 with the rods 12 and 14. This is because the locking segments 326 on the sleeves 300 of the fasteners 46 and 48 (FIG. 4) move radially outward into engagement with the rods 12 and 14, respectively, when each fastener's expander is fully screwed into the fastener's sleeve. The engagement between the fasteners 46 and 48 and the rods 12 and 14 blocks movement of the fasteners 46 and 48 relative to the rods. The radial movement of the locking segments 326 of the fasteners also causes the rods to be clamped against the cylindrical surfaces 181 and 185 which define the rod passages 180 and 182, respectively in the second plate 32. As a result, the expanded fasteners 46 and 48 block movement of the second plate relative to the rods 12 and 14.

The first plate 30, in contrast, is movable relative to the rods 12 and 14, because the second and third fastener openings 110 and 130 are spaced apart from the rod passages 80 and 82. Therefore, the first plate 30 is movable relative to the second plate 32.

Accordingly, the first vertebra V1 is movable vertically downward relative to the second vertebra V2. This relative movement allows for the maintaining of a load on bone graft placed between the vertebrae V1 and V2. If the first plate 30 were not movable vertically downward relative to the second plate 32, then the distance between the vertebrae V1 and V2 would be fixed. If bone graft were placed between the vertebrae V1 and V2 and the bone graft resorbed sufficiently, the bone graft could possibly shrink out of engagement with one or both of the vertebrae V1 and V2. Allowing relative movement of the plates 30 and 32 can help to maintain a load on bone graft placed between the vertebrae V1 and V2 and maintains the vertebrae in contact with the bone graft to facilitate bone growth. The lips 150 and 250 on the plates 30 and 32 are, preferably, configured so that the lips do not contact bone graft placed between the vertebrae.

The caps 50 and 54 on the rods 12 and 14, respectively, limit movement of the first vertebra V1 in a direction away from the second vertebra V2. This helps to maintain the vertebrae V1 and V2 in contact with the bone graft.

Figure 9:
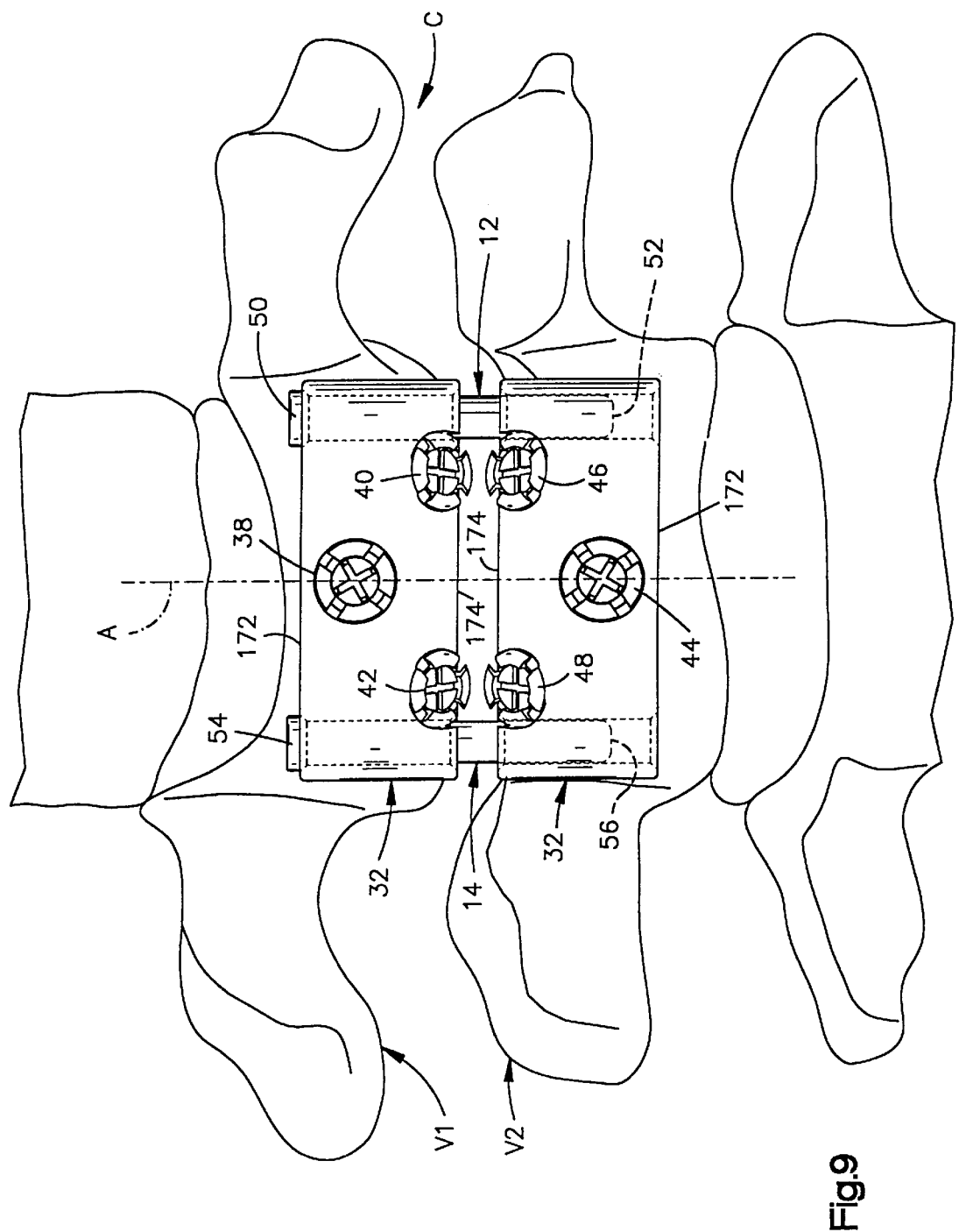
FIG. 9 is a view similar to FIG. 1 of a second embodiment of the invention.

It may not be necessary or desirable, in some circumstances, to use a dynamic (movable) plate such as the plate 30. In such circumstances, two locking plates identical to the plate 32 can be used in the same apparatus 10. Such a system is illustrated in FIG. 9. The upper plate 32 (FIG. 9) is fixed in position relative to the vertebra V1 and to the rods 12 and 14. The lower plate 32 (FIG. 9) is fixed in position relative to the vertebra V2 and to the rods 12 and 14. Accordingly, the apparatus 10 (FIG. 9) blocks relative movement between the vertebrae V1 and V2.

Since the rods 12 and 14 are located at the opposite sides of the plates 30, 32 where the plates curve around the vertebra, the rods 12 and 14 may have a relatively larger diameter, than if the rods 12 and 14 were otherwise located, without creating an excessively high profile for the apparatus 10. This minimizes the chance of contact between the apparatus 10 and parts of the body such as the esophagus. Also, since the fasteners are located between the rods, the fasteners are more easily installed than if the fasteners were otherwise located, for example, if the rods were located between the fasteners.

Figure 10:
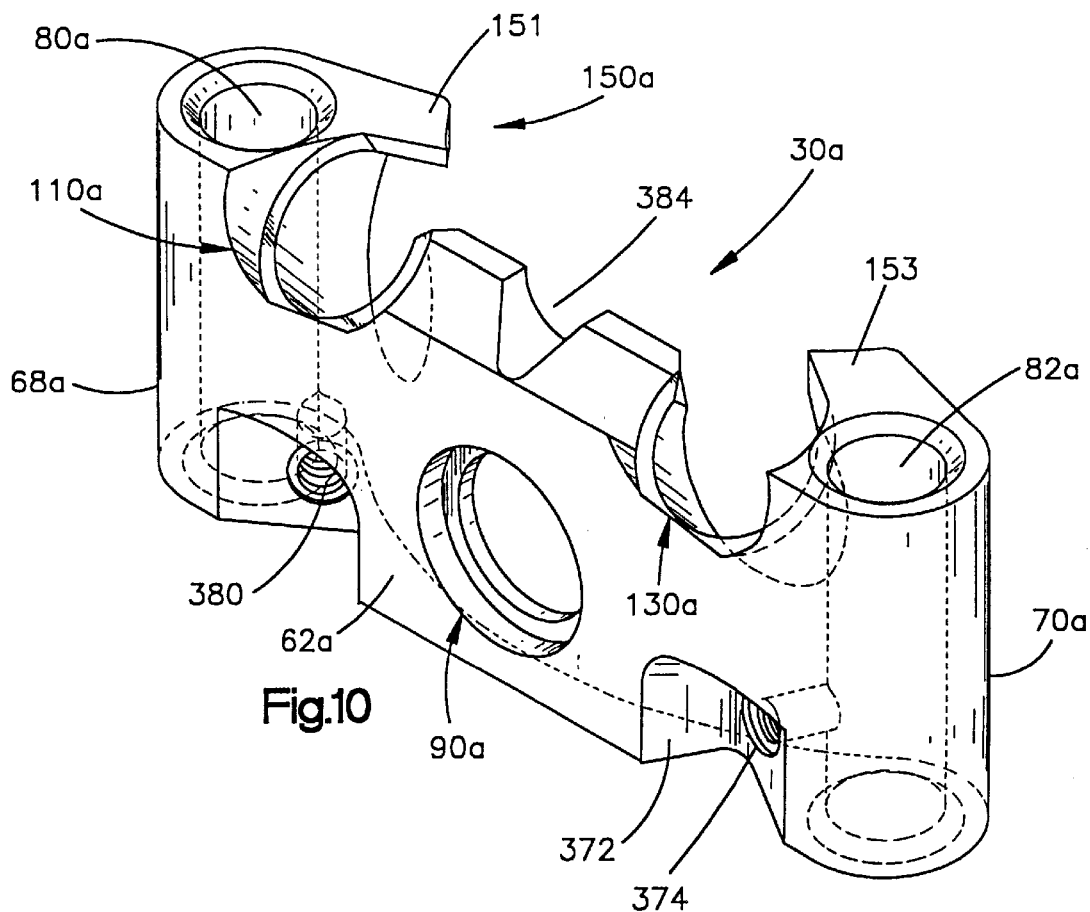
FIG. 10 is a perspective view of a plate which is constructed in accordance with a third embodiment of the present invention.
Figure 11:
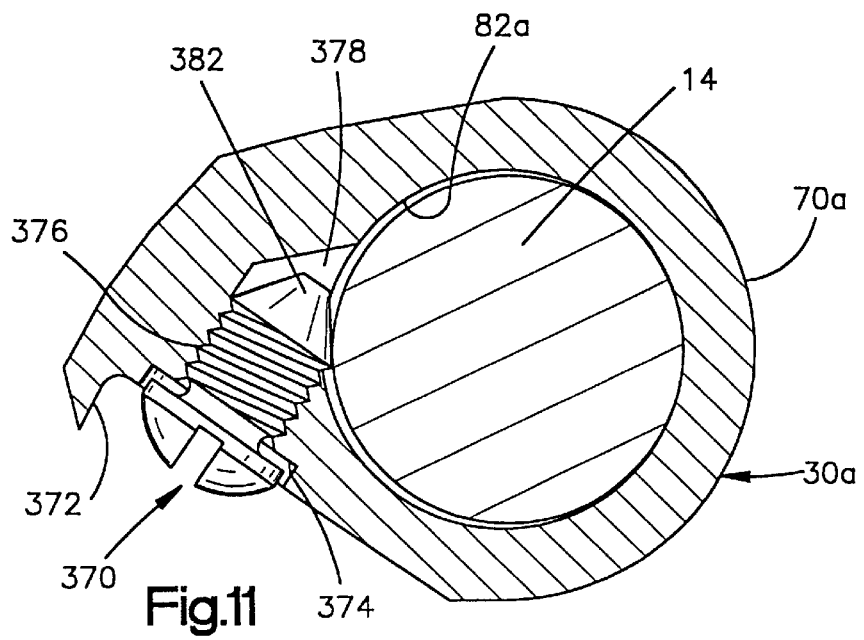
FIG. 11 is an enlarged sectional view of a portion of the plate of FIG. 10 and showing a set screw and rod associated with the plate.

FIGS. 10 and 11 illustrate a plate 30*a* which is constructed in accordance with another embodiment of the present invention. The plate 30*a* can be substituted, in the apparatus 10, for the plate 30. The plate 30*a* is generally similar to the plate 30 (FIGS. 5 and 6), and similar reference numerals are used to designate similar parts, with the suffix "a" added in FIGS. 10 and 11 for clarity.

In the plate 30*a*, a pair of set screws 370 are provided for engaging the rods 12 and 14 to block movement of the plate, and thereby its associated bone portion, relative to the rods. Specifically, the outer side surface 62*a* of the plate 30*a* is recessed at 372 adjacent to the second rod passage 82*a*. A seat 374 extends inwardly from the recess 372 to a threaded opening 376. An inner end portion 378 of the opening 376 intersects with the second rod passage 82*a*. On the opposite side portion 68*a* of the plate 30*a*, a second threaded opening 380 intersects the first rod passage 80*a*.

After the plate 30*a* is assembled with the rods 12 and 14 and positioned adjacent to the spinal column C, fasteners such as the fasteners 38–42 are inserted through fastener openings 90*a*, 110*a*, and 130*a* in the plate 30*a*, to secure the plate to its associated bone portion. The head end portions of the fasteners for the plate 30*a* do not engage the rods 12 and 14, and do not clamp the rods against the plate 30*a*.

A set screw 370 is threaded into the opening 376. An inner end portion 382 of the set screw 370 engages the cylindrical outer surface of the second rod 14. The engagement of the set screw 370 with the second rod 14 clamps the rod against the second side portion 70*a* of the plate 30*a*. Another set screw 370 is threaded into the opening 380 to engage the first rod 12 and clamp the first rod against the first side portion 68*a* of the plate 30*a*.

As a result, the set screws 370, the rods 12 and 14, and the plate 30*a* are interlocked. The plate 30*a* is not movable relative to (along the length of) the rods 12 and 14. Because the plate 30*a* is fixed to its associated bone portion, then the bone portion also is not movable relative to the rods 12 and 14.

In the plate 30*a*, a portion of the lip 150*a* is removed at the location of the fastener openings 110*a* and 130*a*, to provide better visibility. This provides two lip segments 151 and 153 at the side portions 68a and 70a, respectively, of the plate 30a. A portion of the lip 150a also is removed at the lateral center of the plate 30a, and a notch 384 is provided in the plate 30a, again to increase visibility. The lip segments 151 and 153 are spaced apart on opposite sides of the longitudinal axis, or centerline, of the plate 30a.

Figure 12:
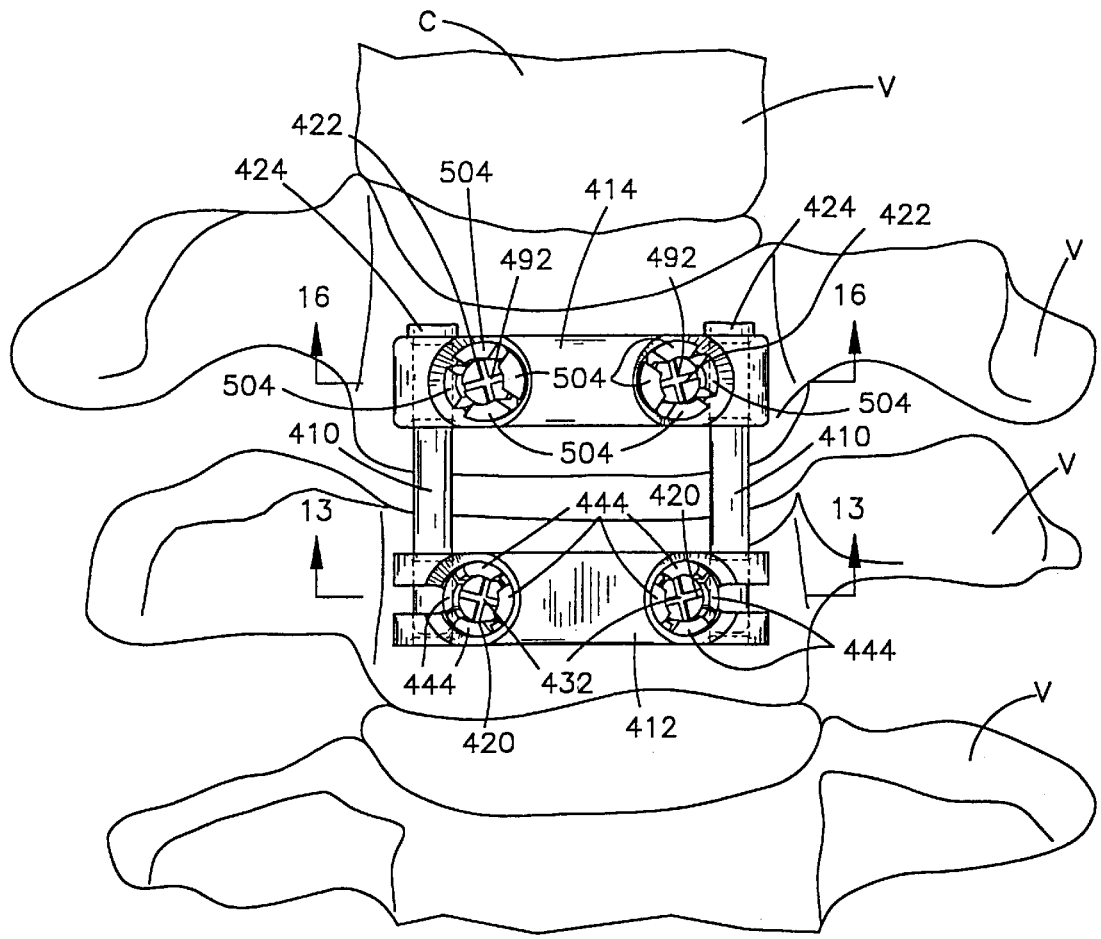
FIG. 12 is a view of a cervical portion of a spinal column with a fourth embodiment of an apparatus constructed in accordance with the present invention connected to anterior portions of the cervical vertebrae to retain a desired spatial relationship between the cervical vertebrae.

FIGS. 12–22 illustrate apparatus which include rods interconnected by a pair of plates each secured to a respective vertebra by two screws. Specifically, FIG. 12 illustrates an apparatus which includes a pair of surgically implantable rods 410 for stabilizing a human spinal column C. The rods 410 are connected to anterior portions of cervical vertebrae V of the spinal column by plates or members 412 and 414. Each rod 410 is elongate and has a circular cross section taken in a plane extending perpendicular to the longitudinal central axis of the rod. The rods 410 are bendable in any desired plane to conform to a desired curvature of the spinal column C. The rods 410 have sufficient strength and rigidity to maintain the vertebrae V in the desired relationship. The rods 410 are made of a biocompatible material such as titanium or stainless steel.

Each of the rods 410 has a length which is at least sufficient to enable the rod to span at least two of the cervical vertebrae v. In the embodiment of the invention illustrated in FIG. 12, the rods 410 span two vertebrae V. Of course, the length of the rods 410 will depend upon the condition to be corrected and the number of vertebrae V to be held in a desired spatial relationship relative to each other by the rods 410.

Figure 13:
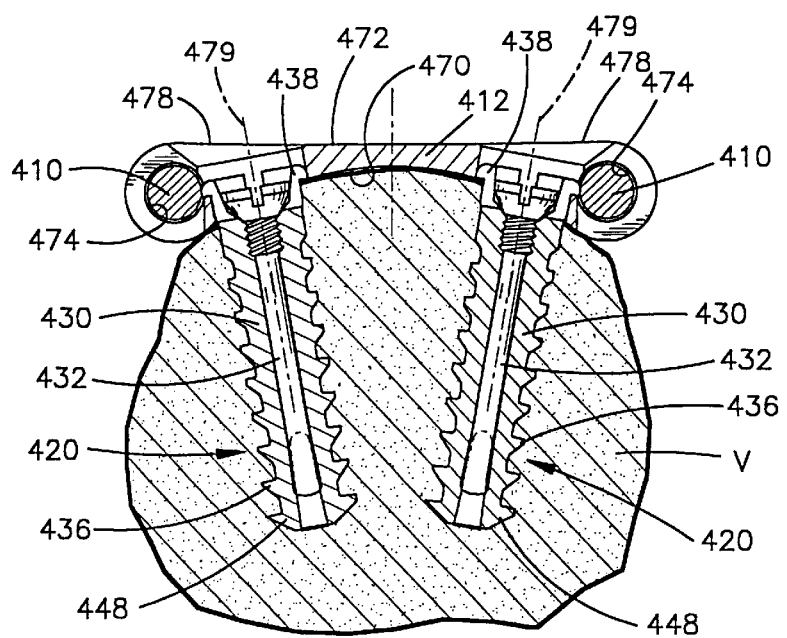
FIG. 13 is a sectional view, taken generally along the line 13—13 of FIG. 12.
Figure 14:
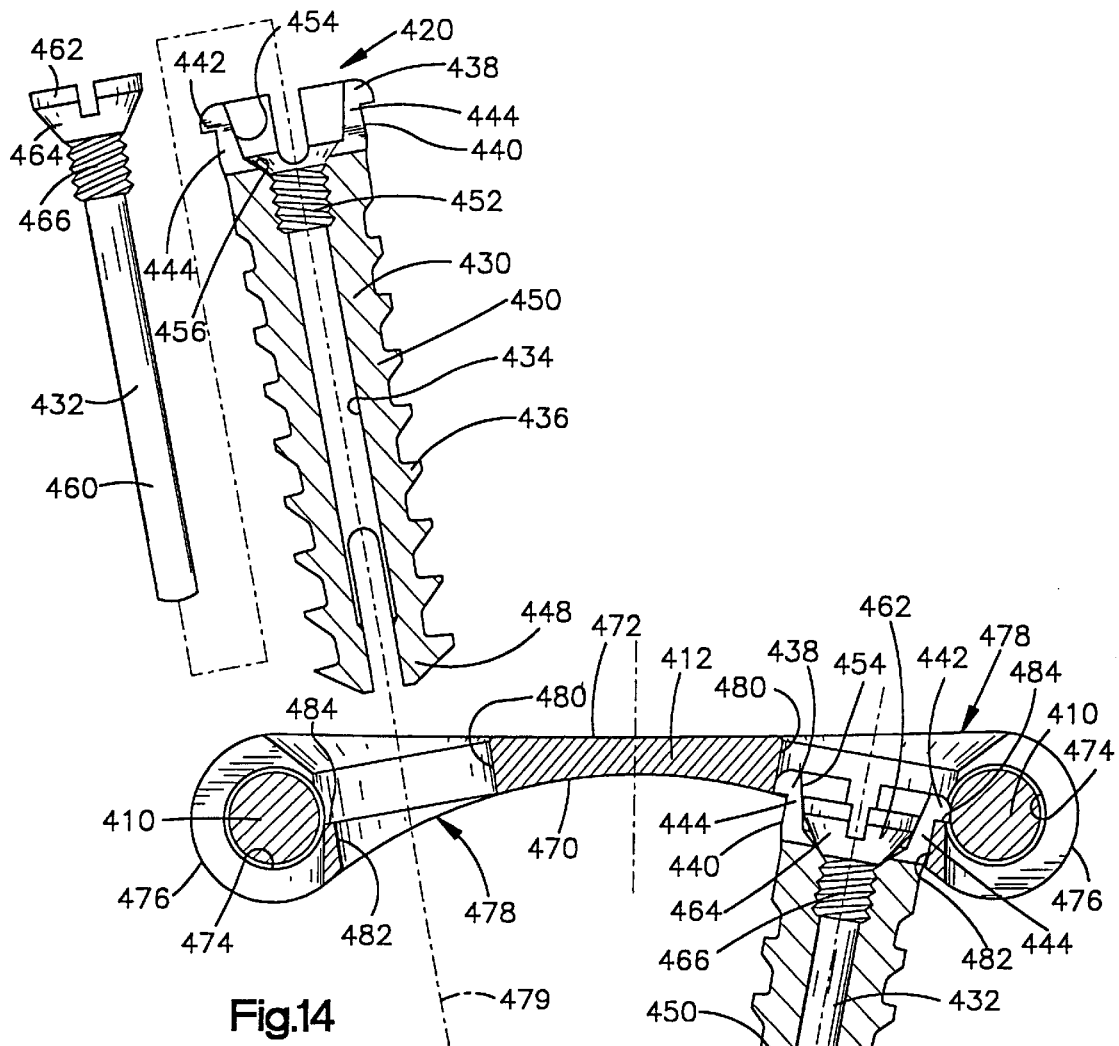
FIG. 14 is an enlarged exploded view of parts of FIG. 12.
Figure 15:
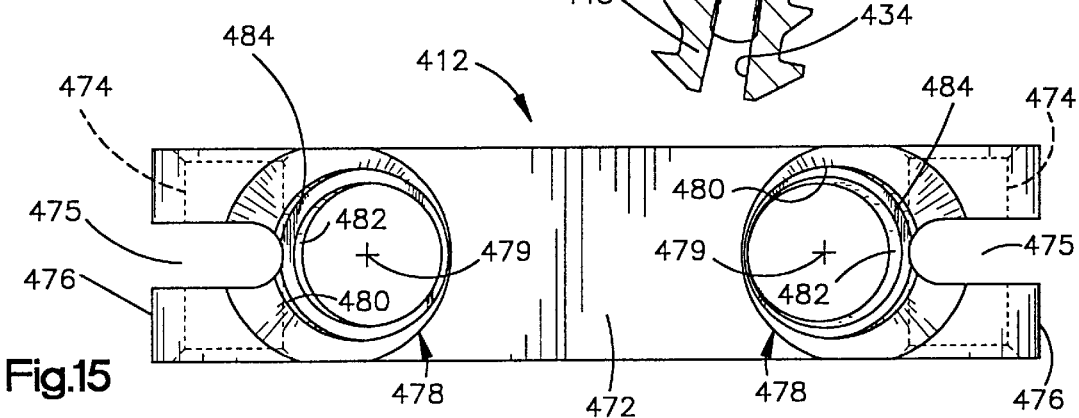
FIG. 15 is a plan view of a part shown in FIG. 14.
Figure 17:
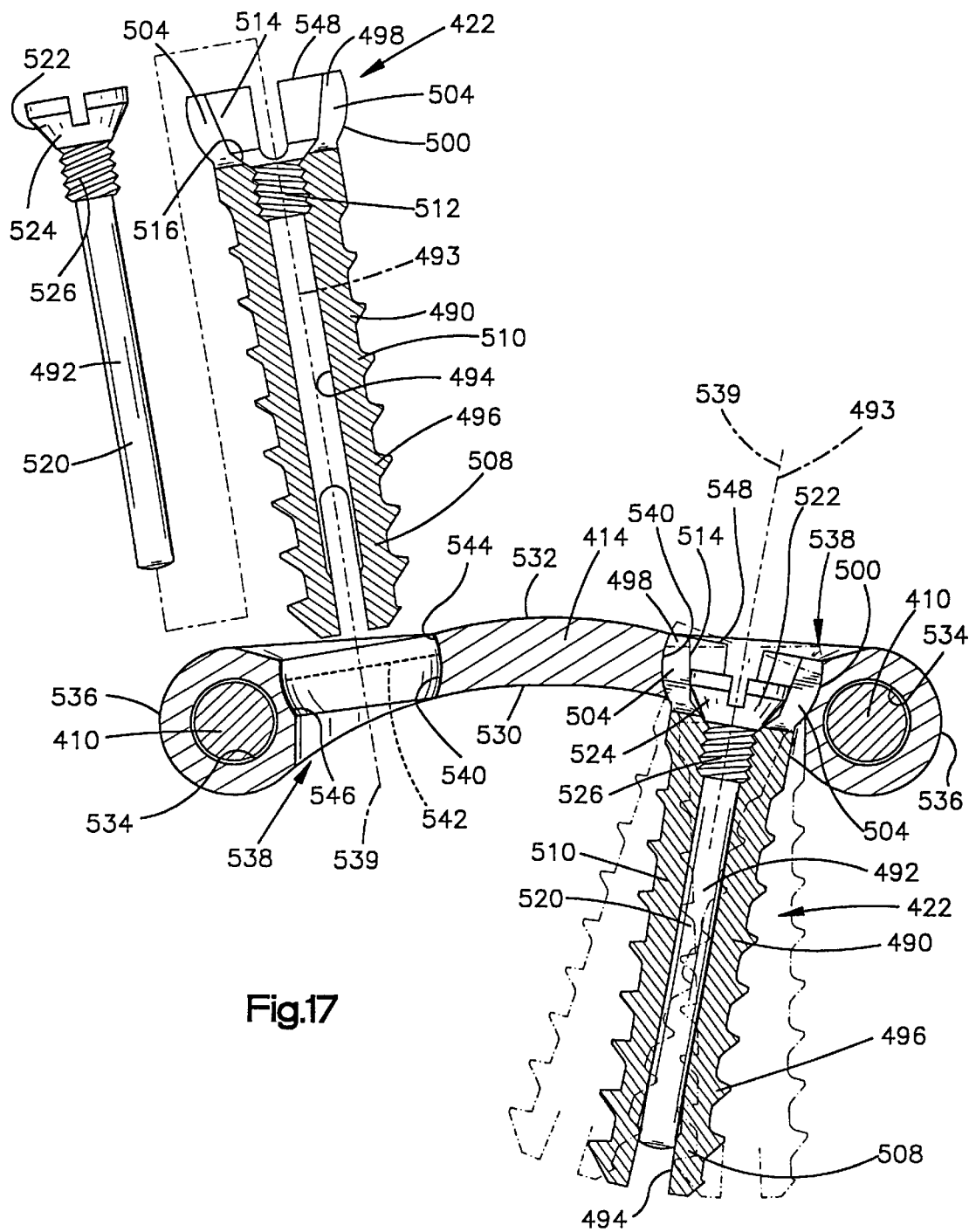
FIG. 17 is an enlarged exploded view of parts of FIG. 16.
Figure 18:
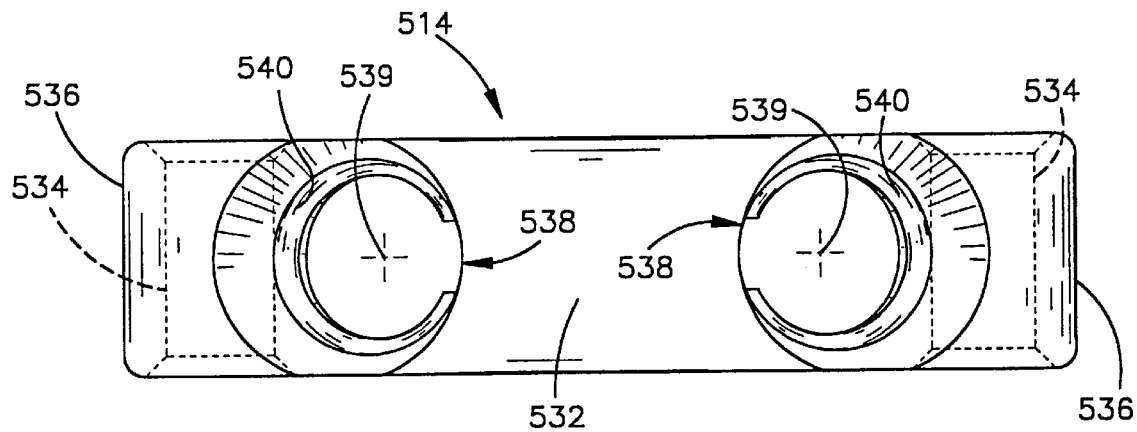
FIG. 18 is a plan view of a part shown in FIG. 17.

The plate 412 is connected to a vertebra V by fasteners 420 (FIG. 13). The fasteners 420 also fix or lock the rods 410 relative to the plate 412 to prevent relative movement between the rods 410 and the plate. The plate 414 is connected to a vertebra V by fasteners 422 (FIG. 16). The fasteners 422 permit relative movement between the plate 414 and the rods 410. Therefore, the plate 414 is considered a dynamic plate.

Each rod 410 terminates in a cap 424 engageable with the plate 414. The caps 424 prevent movement of the plate 414 relative to the rods 410 in a direction away from the plate 412, while allowing movement of the plate 414 in a direction toward the plate 412.

Each of the fasteners 420 (FIGS. 13 and 14) includes a sleeve 430 and an expander 432 located within the sleeve. The sleeve 430 has an axially extending central opening 434 for receiving the expander 432. The sleeve 430 includes a coarse external helical thread convolution 436 for engaging a vertebra V.

The sleeve 430 (FIG. 14) has a head end portion 438 with a cylindrical outer side surface 440. An annular lip or rim 442 extends around the head end portion 438 of the sleeve 430 and projects radially outward from the cylindrical outer side surface 440. The head end portion 438 of the sleeve 430 is radially and axially slotted to define four segments 444 (FIG. 12) of the head end portion 438. The four segments 444 are movable radially outward relative to each other. Thus, the head end portion 438 is expandable. The radially and axially extending slots in the head end portion 438 receive a driving tool for threading the sleeve 430 into a vertebra. An end portion 448 (FIG. 14) of the sleeve 430 opposite from the head end portion 438 is radially and axially slotted to permit radially outward expansion of the end portion 448.

The opening 434 of the sleeve 430 has a first diameter located along a central portion 450 of the sleeve 430 and a second diameter smaller than the first diameter located adjacent the end portion 448. The sleeve 430 has an internally threaded portion 452 between the central portion 450 and the head end portion 438. The head end portion 438 has a conical-shaped surface 454 that tapers from a larger diameter to a smaller diameter adjacent another conical-shaped surface 456. The surface 456 interconnects the surface 454 and the threaded portion 452. The surface 456 tapers from the larger diameter adjacent the surface 454 to the smaller diameter of the threaded portion 452.

The expander 432 has a rod-shaped portion 460 for extending in the opening 434. The rod portion 460 has a diameter which is approximately equal to the diameter of the opening 434 in the central portion 450 of the sleeve. The rod portion 460 engages the interior of the end portion 448 of the sleeve 430 and causes the end portion 448 to expand and help retain the fastener 420 in the vertebra V.

The expander 432 has a head end portion 462 with an X-shaped driver slot for receiving a driving tool for rotating the expander relative to the sleeve 430. The head end portion 462 has a tapering surface 464 for engaging the tapering surface 454 of the sleeve 430. The expander 432 includes a threaded portion 466 for threadably engaging the threaded portion 452 of the sleeve 430. The tapering surface 464 of the expander 432 engages the tapering surface 454 of the sleeve 430 to move the four segments 444 radially outward. Therefore, the head end portion 438 of the sleeve 430 expands.

The member or plate 412 (FIGS. 13–15) is made of a suitable biocompatible material, such as titanium or stainless steel. The plate 412 includes a surface 470 for engaging an anterior surface of the vertebra V and a surface 472 opposite from the surface 470 for facing away from the vertebra V. The plate 412 has generally parallel openings 474 for receiving the rods 410. Slots 475 (FIG. 15) extend from side surfaces 476 of the plate 412 and intersect the openings 474. The slots 475 define a pair of axially spaced arcuate surfaces that engage portions of the rod 410 at axially spaced locations.

The plate 412 (FIGS. 14 and 15) has a pair of openings 478 for receiving the fasteners 420 located adjacent the side surfaces 470 and intersecting the openings 474. The openings 478 have axes 479 that extend at an angle relative to each other. Each of the fastener openings 478 is partially defined by a larger diameter cylindrical surface 480 which extends parallel to the axis 479 of the fastener opening. The fastener opening 478 is partially defined by a smaller diameter cylindrical surface 482 which extends parallel to the axis 479 of the opening. An annular shoulder surface 484 extends radially between the surfaces 480 and 482. The shoulder surface 484 defines a seat or recess in the opening 478 against which the rim 442 of the sleeve 430 engages. The axes 479 of the openings 478 extend at an angle relative to each other so that the fasteners 420 extend at an angle to each other.

When the plate 412 is to be connected to the anterior portion of the cervical vertebra V, it is positioned on the anterior portion of the cervical vertebra with the surface 470 facing the anterior portion of the vertebra V and the rods 410 extending through the openings 474. The sleeves 430 of the fasteners 420 are placed through the openings 478 in the plate 412 and threaded into the vertebra V. The sleeves 430 are threaded into the vertebra V until the rim 442 of the sleeve engages the shoulder surface 484 and presses the surface 470 of the plate 412 against the vertebra V. The expanders 432 are threaded into the sleeves 430 to cause the head end portions 438 to expand so that the segments 444 expand radially outward into engagement with the cylindrical surfaces 480 of the openings 478. The head end portion 438 also expands into engagement with the rod 410 and clamps the rod in the opening 474. Accordingly, the fasteners 420, the plate 412, and the rods 410 are prevented from moving relative to each other.

When the apparatus is positioned on the spinal column C, the fasteners 420 secure the plate 412 to the vertebra v. The plate 412 is also fixed in position relative to the rods 410, as described above. Accordingly, the vertebra connected to the plate 412 is fixed in position relative to the rods 410.

Each of the fasteners 422 (FIGS. 16 and 17) which secure the plate 414 to a vertebra V includes a sleeve 490 and an expander 492 located within the sleeve. Each fastener 422 has a longitudinal central axis 493. The sleeve 490 has an axially extending central opening 494 for receiving the expander 492. The sleeve 490 includes a coarse external helical thread convolution 496 for engaging a vertebra v.

The sleeve 490 (FIG. 17) has a head end portion 498 with a part spherical outer side surface 500. The head end portion 498 of the sleeve 490 is radially and axially slotted to define four segments 504 (FIG. 12) of the head end portion 498. The four segments 504 are movable radially inward and outward relative to each other so that the head end portion 498 is expandable and collapsible. The radially and axially extending slots in the head end portion 498 receive a driving tool for threading the sleeve 490 into a vertebra V. An end portion 508 (FIG. 17) of the sleeve 490 opposite from the head end portion 498 is radially and axially slotted to permit radially outward expansion of the end portion 508. The head end portion 498 of the fastener 422 has a surface 548 facing away from the end portion 508.

The opening 494 of the sleeve 490 has a first diameter located along a central portion 510 of the sleeve 490 and a second diameter smaller than the first diameter located adjacent the end portion 508. The sleeve 490 has an internally threaded portion 512 between the central portion 450 and the head end portion 498. The head end portion 498 has a conical-shaped surface 514 that tapers from a larger diameter to a smaller diameter adjacent another conical-shaped surface 516. The surface 516 interconnects the surface 514 and the threaded portion 512. The surface 516 tapers from the larger diameter adjacent the surface 514 to the smaller diameter of the threaded portion 512.

The expander 492 has a rod-shaped portion 520 for extending into the opening 494. The rod portion 520 has a diameter which is approximately equal to the diameter of the opening 494 in the central portion 510 of the sleeve 490. The rod portion 520 engages the interior of the end portion 508 of the sleeve 490 and causes the end portion 508 to expand and help retain the fastener 422 in the vertebra V.

The expander 492 has a head end portion 521 with an X-shaped driver slot for receiving a driving tool for rotating the expander relative to the sleeve 490. The head end portion 522 has a tapering surface 524 for engaging the tapering surface 514 of the sleeve 490. The expander 492 includes a threaded portion 526 for threadably engaging the threaded portion 512 of the expander 490. The tapering surface 524 of the expander 492 engages the tapering surface 514 of the sleeve 490 to move the four segments 504 radially outward. Therefore, the head end portion 498 of the sleeve 490 expands.

The member or plate 414 (FIGS. 16–18) is made of a suitable biocompatible material, such as titanium or stainless steel. The plate 414 includes a surface 530 for engaging an anterior surface of the vertebra V and a surface 532 opposite from the surface 530 for facing away from the vertebra V. The plate 414 has generally parallel rod openings 534 for receiving the rods 410. The plate 414 has a pair of fastener openings 538 for receiving the fasteners 422 located adjacent side surfaces 536 of the plate 414. The openings 538 have axes 539 extending at an angle to each other.

Each fastener opening 538 is partially defined by a part spherical surface 540 (FIGS. 17–21) centered on the axis 539. The part spherical surface 540 defines a seat or recess in the opening 538 against which the part spherical surface 500 of the sleeve 490 engages.

The part spherical recess 540 has a major diameter 542. A first portion 544 of the recess 540 is located on one side of the major diameter 542 and adjacent the surface 532 of the plate 414. A second portion 546 of the recess 540 is located on the other side of the major diameter 542 and adjacent the surface 530 of the plate 414.

When the plate 414 is to be connected to a vertebra V, the plate 414 is placed on the vertebra V with the surface 530 engaging the anterior portion of the vertebra V and the rods 410 extending through the openings 534. The sleeves 490 are threaded into the vertebra V through the openings 538 in the plate 414. As the head end portion 498 of the sleeve 490 enters the opening 538 in the plate 414 the segments 504 are compressed radially inward then expand radially outward. The surfaces 548 on the head end portions 498 are located in the first portions 544 of the recesses 540 when the head end portions 498 are received in the recesses. Because the major diameter 542 of each recess 540 is spaced inward from the outer surface 532 of the plate 414, the expanded fasteners 422 resist movement out of the recesses in the plate.

Figure 19:
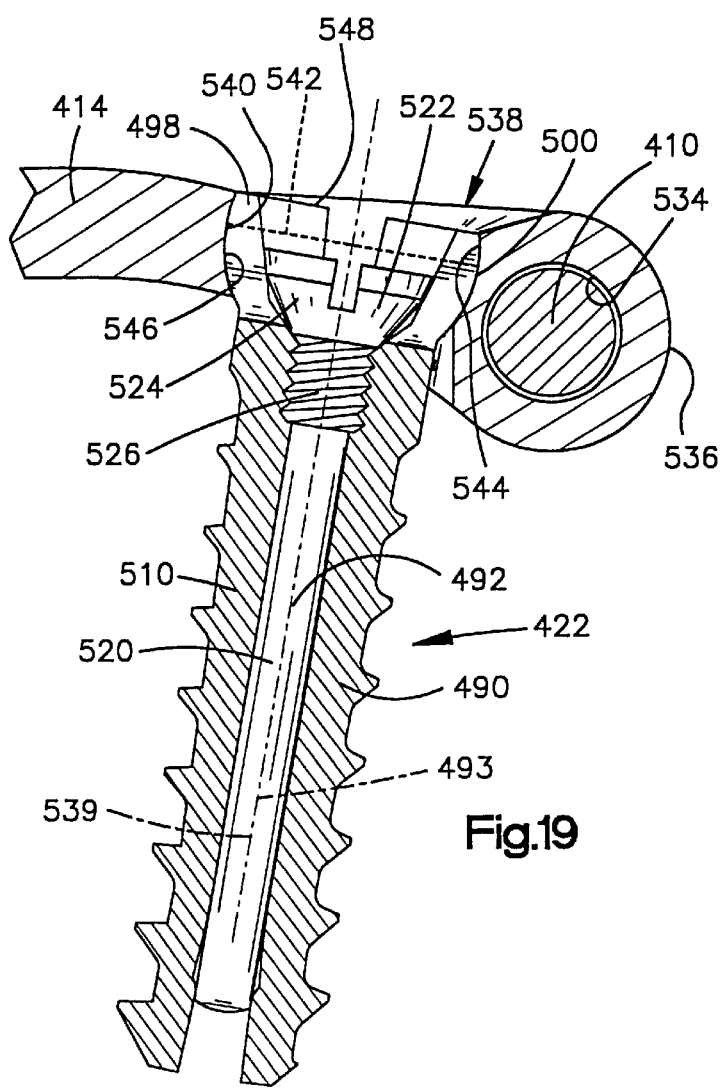
FIG. 19 is an enlarged view of parts of FIG. 17.

The expander 492 is threaded into the sleeve 490 and causes the head end portion 498 to expand into engagement with the opening 538 and prevent relative movement between the plate 414 and the fastener 422. The engagement of the part spherical surfaces 500 of the sleeves 490 with the part spherical surfaces 540 of the openings 538, enables the fasteners 422 to have a plurality of positions in which the axis 493 of each fastener 422 extends at an angle to the axis 539 of its associated opening 538 in any direction. Preferably, the axis 493 of each fastener 422 can be positioned at a maximum of approximately 10° in any direction relative to the axis 539 of its associated opening 538. Three alternative positions are shown in FIGS. 19–21.

The fasteners 422 secure the plate 414 to the vertebra V. However, the plate 414 is movable relative to the rods 410. Accordingly, the vertebra V connected to the plate 414 is movable relative to the rods 410 along the longitudinal axes of the rods.

Accordingly, the vertebra V corrected to the plate 414 is movable vertically downward toward the vertebra that the plate 412 is connected to. This relative movement allows for the maintaining of a load on bone graft placed between the vertebrae V. If the plate 414 was not movable relative to the plate 412, then the distance between the vertebrae V would be fixed. If a bone graft is placed between the vertebrae V and the bone graft resorbed sufficiently, the bone graft could possibly shrink out of engagement with one or both of the vertebrae V. Allowing relative movement of the plates 412 and 414 can help to maintain a desired load on bone graft placed between the vertebrae V and maintain the vertebrae in contact with the bone graft to facilitate bone growth.

It may not be necessary, in some circumstances, to use a dynamic (movable) plate such as the plate 414. In such circumstances, two plates identical to the plate 412 can be used in the same apparatus. Such a system is illustrated in FIG. 22.

In FIG. 22 a pair of surgically implantable rods 560 are connected to anterior portions of cervical vertebrae V of a spinal column C by a pair of identical plates or members 562. The plates 562 are identical to the plates 412 illustrated in FIGS. 12–14 and will not be described in detail. The plates 562 are connected to the vertebrae V by fasteners 564. The fasteners 564 are identical to the fasteners 420 illustrated in FIGS. 12–14 and will not be described in detail. The fasteners 564 also fix the rods 560 relative to the plates 562 to prevent relative movement between the rods and the plates. The apparatus illustrated in FIG. 22 prevents relative movement between the vertebrae V since the plates 562 and rods 560 are prevented from moving relative to each other by the fasteners 564.

Figure 23:
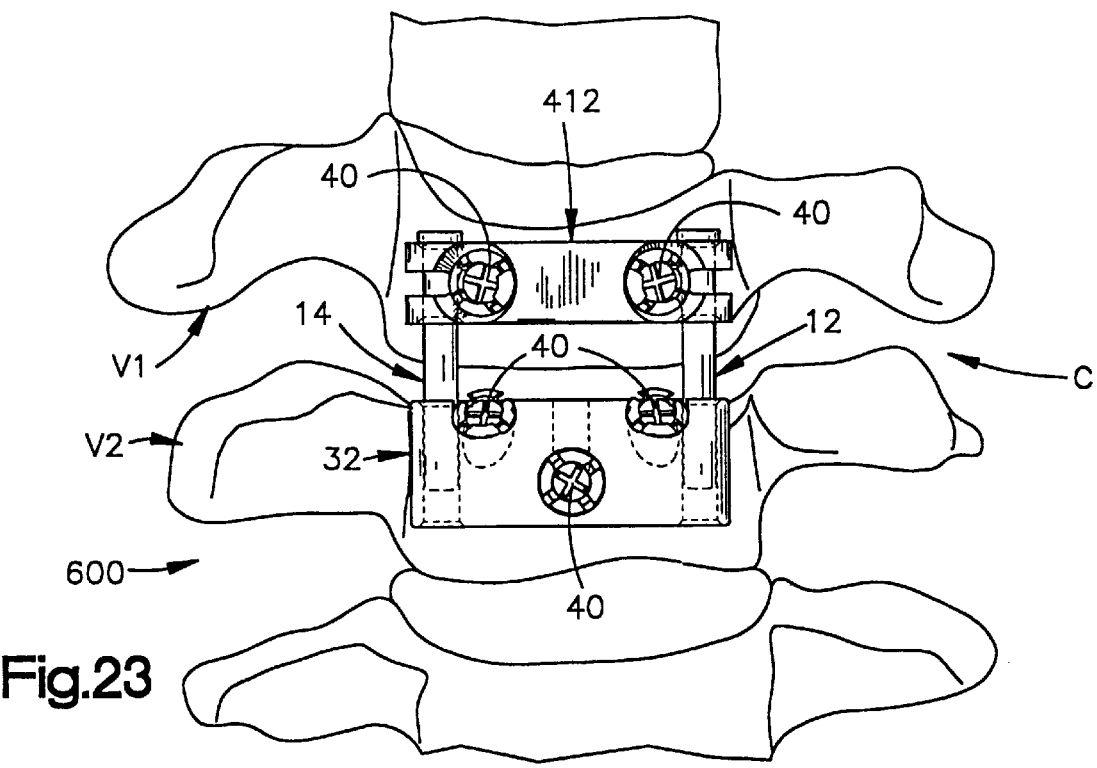
FIG. 23 is a view similar to FIG. 1 of an apparatus which is constructed in accordance with a sixth embodiment of the present invention.

FIG. 23–26 illustrate several embodiments which include one plate secured to one vertebra by two screws and another plate secured to another vertebra by three screws. Specifically, FIG. 23 illustrates an apparatus 600 which includes a 2-screw plate 412 which is the same as the plate 412 described in detail with reference to FIGS. 12–22. The plate 412 is fastened to the vertebra V1 with a pair of fasteners 40. The fasteners 40 (FIG. 23) are the same as the fasteners which are described in detail with reference to FIGS. 1–11. The fasteners 40 (FIG. 23) have head end portions which are expanded into engagement with the rods 12 and 14. As a result, the plate 412 is blocked from movement relative to the rods 12 and 14, when the plate is secured to the vertebra V1.

The apparatus 600 also includes a plate 32 which is the same plate which is described in detail with reference to FIGS. 1–8. The plate 32 is fastened to the vertebra V2 with three fasteners 40. The fasteners 40 are the same as the fasteners which are described in detail with reference to FIGS. 1–11. The fasteners 40 (FIG. 23) have head end portions which are expanded into engagement with the rods 12 and 14. As a result, the plate 32 is blocked from movement relative to the rods 12 and 14, when the plate is secured to the vertebra V2.

Therefore, when the apparatus 600 is installed on the spinal column C, both plates 32 and 412 are fixed in position relative to the rods. Both vertebrae V1 and V2 are thus fixed in position relative to the rods 12 and 14. This blocks relative movement between the vertebrae V1 and V2.

Figure 24:
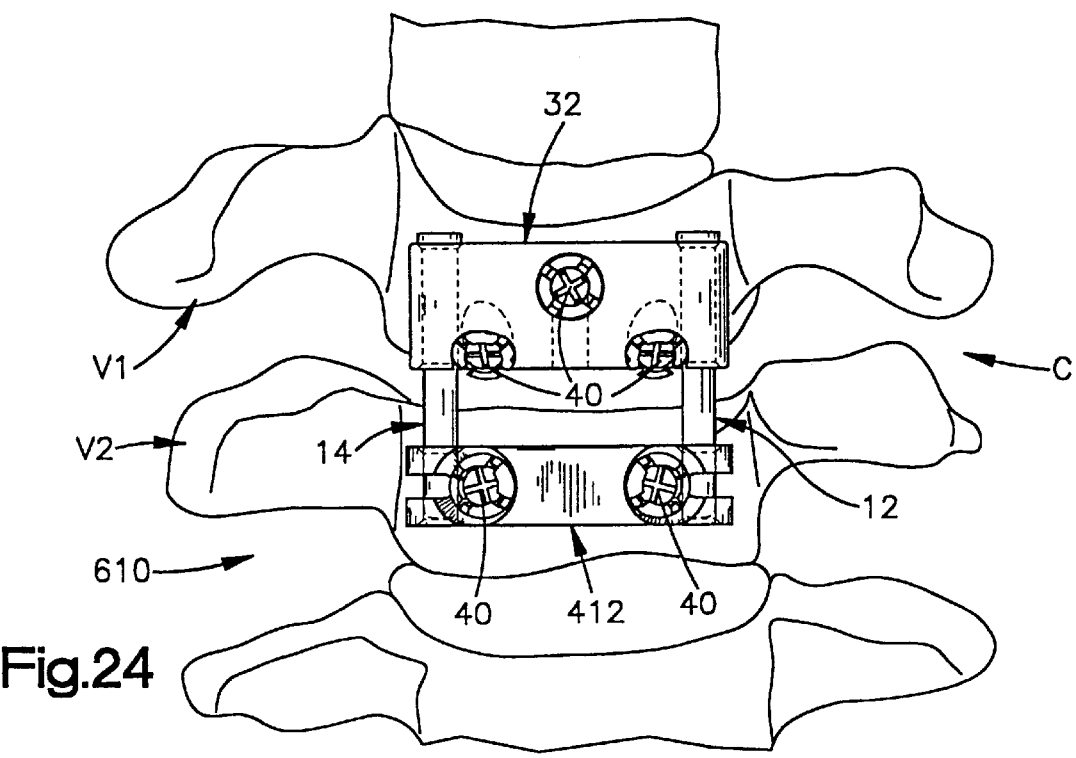
FIG. 24 is a view similar to FIG. 1 of an apparatus which is constructed in accordance with a seventh embodiment of the present invention.

FIG. 24 illustrates an apparatus 610 in which the relative positions of the plates 412 and 32 are reversed as compared to the positions of the plates in FIG. 20. The apparatus 610 (FIG. 24) is, otherwise, identical to the apparatus 600 (FIG. 23). As a result, the apparatus 610 blocks relative movement between the vertebrae V1 and V2.

Figure 25:
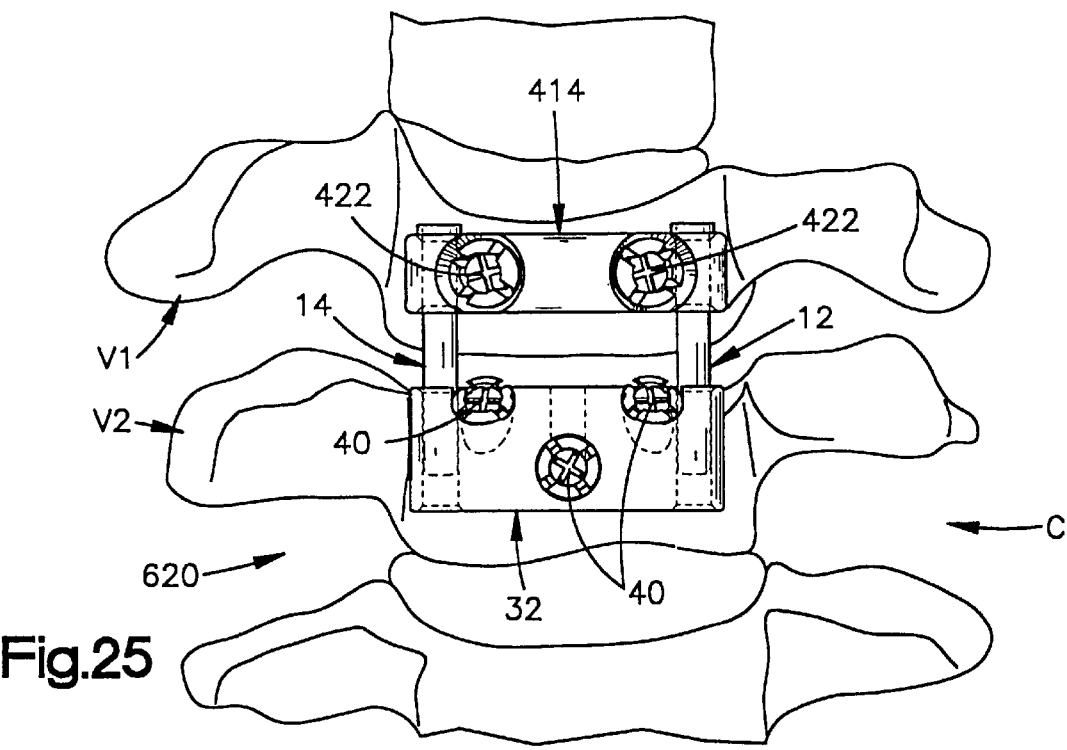
FIG. 25 is a view similar to FIG. 1 of an apparatus which is constructed in accordance with an eighth embodiment of the present invention.

FIG. 25 illustrates an apparatus 620 which includes a plate 414 which is the same as the plate 414 described in detail with reference to FIGS. 12–22. The plate 414 is fastened to the vertebra V1 with a pair of fasteners 422. The fasteners 422 (FIG. 25) are the same as the fasteners 422 which are described in detail with reference to FIGS. 12–22. The fasteners 422 have head end portions which do not engage the rods 12 and 14. As a result, the plate 414 is movable relative to the rods 12 and 14, when the plate is secured to the vertebra V1.

The apparatus 620 also includes a plate 32 which is the same plate which is described in detail with reference to FIGS. 1–8. The plate 32 is fastened to the vertebra V2 with three fasteners 40. The fasteners 40 (FIGS. 25) are the same as the fasteners 40 which are described in detail with reference to FIGS. 1–11. The fasteners 40 have head end portions which are expanded into engagement with the rods 12 and 14. As a result, the plate 30 is blocked from movement relative to the rods 12 and 14, when the plate is secured to the vertebra V2.

Therefore, when the apparatus 620 is installed on the spinal column C, the plate 414 is movable relative to the plate 32. This allows relative movement between the vertebrae V1 and V2.

Figure 26:
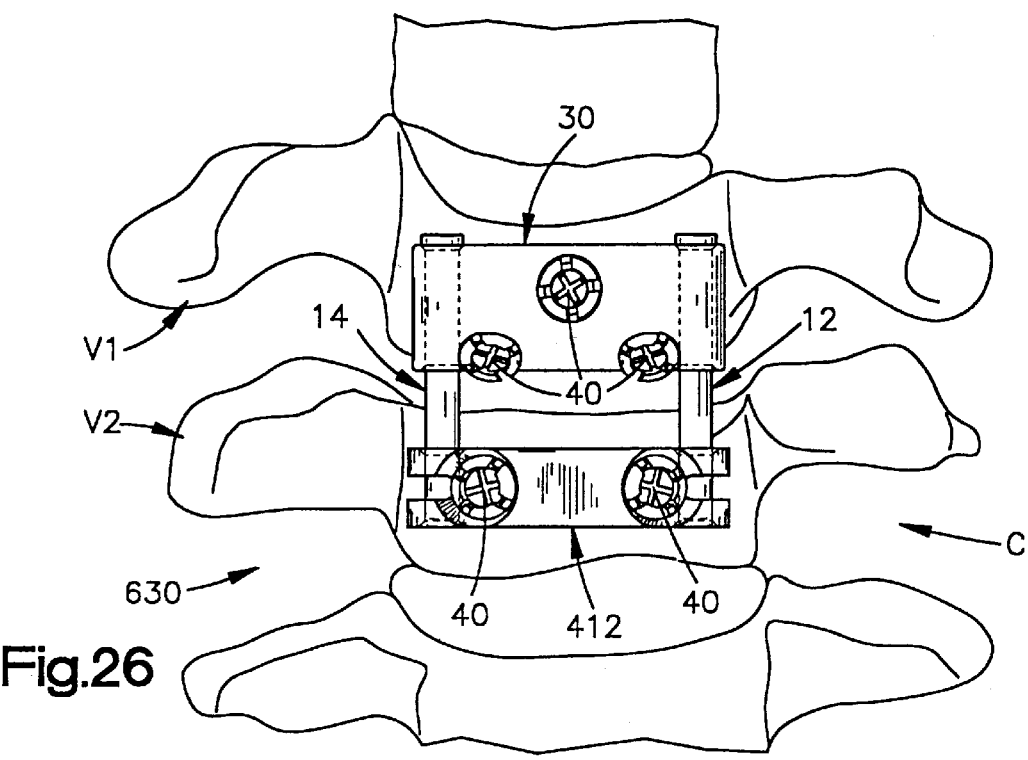
FIG. 26 is a view similar to FIG. 1 of an apparatus which is constructed in accordance with a ninth embodiment of the present invention.

FIG. 26 illustrates an apparatus 630 which includes a plate 412 which is the same as the plate 412 described in detail with reference to FIGS. 12–22. The plate 412 is fastened to the vertebra V2 with a pair of fasteners 40. The fasteners 40 (FIG. 26) are the same as the fasteners 40 which are described in detail with reference to FIGS. 1–8. The fasteners 40 which secure the plate 412 have head end portions which are expanded into engagement with the rods 12 and 14. As a result, the plate 412 is blocked from movement relative to the rods 12 and 14, when the plate is secured to the vertebra V2.

The apparatus 630 also includes a plate 30 which is the same plate which is described in detail with reference to FIGS. 1–8. The plate 30 is fastened to the vertebra V1 with three fasteners 40. The fasteners 40 (FIG. 26) are the same as the fasteners 40 which are described in detail with reference to FIGS. 1–11. The fasteners 40 which secure the plate 30 have head end portions which do not engage the rods 12 and 14. As a result, the plate 30 is movable relative to the rods 12 and 14, when the plate is secured to the vertebra V1. Therefore, when the apparatus 630 is installed on the spinal column C, the plate 30 is movable relative to the plate 412. This allows relative movement between the vertebrae V1 and V2.

From the above description of the invention, those skilled in the art will perceive improvements, changes and modifications in the invention. Such improvements, changes and modifications within the skill of the art are intended to be covered by the appended claims.

What is claimed is:

1. A spine stabilization apparatus comprising:
   a non-threaded longitudinal member including a longitudinal axis and being positionable along the spine;
   a first plate formed to include a first passage, the longitudinal member being fixed within the first passage to couple the first plate in a generally stationary position relative to the longitudinal member;
   a first fastener coupled to the first plate and formed to couple the first plate to the spine;
   a dynamic second plate formed to include a second passage, the longitudinal member being movable within the second passage to permit movement of the dynamic second plate along the longitudinal axis relative to the first plate when the dynamic plate is coupled to the spine; and
   a second fastener coupled to the dynamic second plate and formed to couple the dynamic second plate to the spine.

2. The apparatus of claim 1, wherein the apparatus includes a pair of longitudinal members extending between the first and second plates.

3. The apparatus of claim 2, wherein the first plate is formed to include a pair of first passages formed to receive the respective longitudinal members.

4. The apparatus of claim 3, wherein the second plate is formed to include a pair of second passages formed to receive the respective longitudinal members.

5. A spine stabilization apparatus comprising:
a longitudinal member including a longitudinal axis and being positionable along the spine;
a first plate formed to include a first passage, the longitudinal member being fixed within the first passage to couple the first plate in a generally stationary position relative to the longitudinal member;
a first fastener coupled to the first plate and formed to couple the first plate to the spine;
a second plate formed to include a second passage, the longitudinal member being movable within the second passage to permit movement of the second plate alone the longitudinal axis relative to the first plate; and
a second fastener coupled to the second plate and formed to couple the second plate to the spine, and the first fastener engages the longitudinal member in the first passage.

6. The apparatus of claim 5, wherein the first fastener includes a threaded end portion and a second end portion engaging the first plate.

7. An apparatus for retaining first and second vertebrae of a spinal column in a desired spatial relationship, the apparatus comprising:
a longitudinal member including a longitudinal axis and being positionable along the spinal column;
a first plate coupled to the longitudinal member;
a first fastener coupled to the first plate and formed to couple the first plate to the first vertebra, the first fastener engaging the longitudinal member;
a second plate coupled to the longitudinal member and formed for movement relative to the first plate along the longitudinal axis; and
a second fastener coupled to the second plate and formed to couple the second plate to the second vertebra.

8. The apparatus of claim 7, wherein the first plate is formed to include a passage and the longitudinal member extends in the passage.

9. The apparatus of claim 8, further comprising a second longitudinal member coupled to the first and second plates.

10. The apparatus of claim 9, wherein the first plate is formed to include a second passage and the second longitudinal member extends in the second passage.

11. The apparatus of claim 9, wherein the second plate is formed to include first and second passages and the longitudinal members extend in the first and second passages of the second plate respectively.

12. The apparatus of claim 8, wherein the first plate includes an inner side surface that is configured to face the vertebrae, an outer side surface, and opposite end surfaces extending between the outer and inner side surfaces and the passage extends between the opposite end surfaces.

13. The apparatus of claim 7, wherein the first fastener includes a threaded end portion and a second end portion engaging the first plate.

14. The apparatus of claim 13, further comprising at least two first fasteners each having a respective threaded end portion and a respective second end portion in engagement with the first plate.

15. The apparatus of claim 14, further comprising at least two second fasteners each having a respective threaded end portion and a respective second end portion in engagement with the second plate.

16. An apparatus for retaining first and second vertebrae of a spinal column in a desired spatial relationship, the apparatus comprising:
a longitudinal member including a longitudinal axis and being positionable along the spinal column;
a first plate coupled to the longitudinal member;
a first fastener coupled to the first plate and formed to couple the first plate to the first vertebra;
a second plate coupled to the longitudinal member and formed for movement relative to the first plate along the longitudinal axis; and
a second fastener coupled to the second plate and formed to couple the second plate to the second vertebra, and the first fastener includes a threaded end portion and a second end portion engaging the first plate and the second end portion of the first fastener engages the longitudinal member.

17. A spine stabilization apparatus comprising:
non-threaded rods positioned to lie spaced-apart from one another, each rod including a longitudinal axis;
a first plate formed to include first passages, the rods being fixed within the first passages respectively to couple the first plate in a generally stationary position relative to the rods;
fasteners coupled to the first plate and formed to couple the first plate to the spine;
a dynamic second plate formed to include second passages, the rods being movable within the second passages respectively to permit movement of the dynamic second plate along the longitudinal axis relative to the first plate when the dynamic second plate is coupled to the spine; and
second fasteners coupled to the dynamic second plate and formed to couple the dynamic second plate to the spine.

18. A spine stabilization apparatus comprising:
rods positioned to lie spaced-apart from one another, each rod including a longitudinal axis;
a first plate formed to include first passages, the rods being fixed within the first passages respectively to couple the first plate in a generally stationary position relative to the rods;
fasteners coupled to the first plate and formed to couple the first plate to the spine;
a second plate formed to include second passages, the rods being movable within the second passages respectively to permit movement of the second plate along the longitudinal axis relative to the first plate; and
second fasteners coupled to the second plate and formed to couple the second plate to the spine and the first fasteners extend into the first passages respectively and engage the rods.

19. The apparatus of claim 18, wherein the second fasteners extend through the second plate spaced-apart from the second passages.

20. A spine stabilization apparatus comprising:
a non-threaded rod including a longitudinal axis and being positionable along the spine;
a first plate including opposite ends and a first rod passage extending between the opposite ends, the rod being fixed within the first rod passage to couple the first plate in a generally stationary position relative to the rod;
a first fastener coupled to the first plate and formed to couple the first plate to the spine;
a dynamic second plate including opposite ends and a second rod passage extending between the opposite ends of the dynamic second plate, the rod being movable within the second rod passage to permit movement of the dynamic second plate along the longitudinal axis relative to the first plate when the dynamic second plate is coupled to the spine; and
a second fastener coupled to the dynamic second plate and formed to couple the dynamic second plate to the spine.

* * * * *